US010188715B2

(12) United States Patent
Rubio Nistal et al.

(10) Patent No.: US 10,188,715 B2
(45) Date of Patent: Jan. 29, 2019

(54) SWINE DYSENTERY VACCINE

(71) Applicants: AQUILÓN CYL S.L., León (ES); UNIVERSIDAD DE LEÓN, León (ES)

(72) Inventors: Pedro Miguel Rubio Nistal, León (ES); Ana Maria Carvajal Urueña, León (ES); Marta García Díez, León (ES)

(73) Assignees: AQUILON CYL SOCIEDAD LIMITADA, Leon (ES); UNIVERSIDAD DE LEÓN, León (ES)

( * ) Notice: Subject to any disclaimer, the term of this patent is extended or adjusted under 35 U.S.C. 154(b) by 0 days.

(21) Appl. No.: 15/858,166

(22) Filed: Dec. 29, 2017

(65) Prior Publication Data
US 2018/0193441 A1 Jul. 12, 2018

Related U.S. Application Data

(63) Continuation-in-part of application No. 14/900,246, filed as application No. PCT/EP2014/063695 on Jun. 27, 2014, now Pat. No. 9,855,322.

(30) Foreign Application Priority Data

Jun. 28, 2013 (EP) .................................... 13382255
Oct. 24, 2017 (EP) .................................... 17382711

(51) Int. Cl.
| | |
|---|---|
| *A61K 39/02* | (2006.01) |
| *A61K 39/00* | (2006.01) |
| *A61P 31/04* | (2006.01) |
| *C12R 1/01* | (2006.01) |
| *C12N 1/20* | (2006.01) |

(52) U.S. Cl.
CPC .......... *A61K 39/0225* (2013.01); *A61P 31/04* (2018.01); *C12N 1/20* (2013.01); *C12R 1/01* (2013.01); *A61K 2039/521* (2013.01); *A61K 2039/545* (2013.01); *A61K 2039/552* (2013.01)

(58) Field of Classification Search
CPC combination set(s) only.
See application file for complete search history.

(56) References Cited

U.S. PATENT DOCUMENTS

| | | | |
|---|---|---|---|
| 4,100,272 | A | 7/1978 | Glock et al. |
| 5,554,372 | A | 9/1996 | Hunter |
| 8,114,411 | B1 | 2/2012 | Kuo et al. |
| 9,855,322 | B2 | 1/2018 | Rubio Nistal et al. |
| 2004/0033234 | A1 | 2/2004 | Berinstein et al. |

FOREIGN PATENT DOCUMENTS

| | | | |
|---|---|---|---|
| CN | 102281893 | A | 12/2011 |
| WO | 1991/06316 | A1 | 5/1991 |
| WO | 1995/01805 | A1 | 1/1995 |
| WO | 2008/017636 | A2 | 2/2008 |

OTHER PUBLICATIONS

David, Help from "friendly" bacteria. Nature Reviews Microbiology. Oct. 2009;7:688.

Diego et al., Serpulina hyodysenteriae challenge of fattening pigs vaccinated with anadjuvanted bivalent bacterin against swine dysentery. Vaccine. May 1995;13(7):663-7.

Hidalgo et al., Multiple-locus variable-number tandem-repeat analysis of the swine dysentery pathogen, Brachyspira hyodysenteriae. J Clin Microbiol. Aug. 2010;48(8):2859-65.
Osorio et al., Dissemination of clonal groups of Brachyspira hyodysenteriae amongst pig farms in Spain, and their relationships to isolates from other countries. PLoS One. 2012;7(6):e39082. 11 pages.
Stone et al., Lipopolysaccharide enhances the cytotoxicity of 2-chloroethyl ethyl sulfide. BMC Cell Biol. Jan. 6, 2003;4:1. 7 pages.
Extended European Search Report for Application No. 13382255.1, dated Dec. 16, 2013.
International Search Report and Written Opinion for Application No. PCT/EP2014/063695, dated Sep. 15, 2014.

*Primary Examiner* — Sarvamangala Devi
(74) *Attorney, Agent, or Firm* — McCarter & English, LLP; Jill Ann Mello

(57) ABSTRACT

The present invention relates to a composition comprising *Brachyspira hyodysenteriae* bacteria, particularly in the field of immunization against swine dysentery. The composition of the invention may comprise bacteria from at least two genetically diverse strains of *B. hyodysenteriae*. The composition of the invention may also comprise bacteria of a strain deposited at the Collection Nationale de Cultures de Microorganismes (CNCM), Institut Pasteur, on Mar. 14, 2013, with registration number CNCM I-4720. The invention relates also to the composition of the invention for use as a vaccine, preferably a universal vaccine against swine dysentery caused by *B. hyodysenteriae*.

10 Claims, 23 Drawing Sheets

Specification includes a Sequence Listing.

A)

B)

```
                          SEQUENCE LISTING

<160> NUMBER OF SEQ ID NOS: 22

<210> SEQ ID NO 1
<211> LENGTH: 25
<212> TYPE: DNA
<213> ORGANISM: Artificial Sequence
<220> FEATURE:
<223> OTHER INFORMATION: Primer sequence Bhyo_6 F

<400> SEQUENCE: 1
aaatataact catattcata acaag                                              25

<210> SEQ ID NO 2
<211> LENGTH: 20
<212> TYPE: DNA
<213> ORGANISM: Artificial Sequence
<220> FEATURE:
<223> OTHER INFORMATION: Primer sequence Bhyo_6 R

<400> SEQUENCE: 2
agagaacttc aaaaaacttc                                                    20

<210> SEQ ID NO 3
<211> LENGTH: 29
<212> TYPE: DNA
<213> ORGANISM: Artificial Sequence
<220> FEATURE:
<223> OTHER INFORMATION: Primer sequence Bhyo_7 F

<400> SEQUENCE: 3
agtaataaat taaaaaatct ctagggtgg                                          29

<210> SEQ ID NO 4
<211> LENGTH: 20
<212> TYPE: DNA
<213> ORGANISM: Artificial Sequence
<220> FEATURE:
<223> OTHER INFORMATION: Primer sequence Bhyo_7 R

<400> SEQUENCE: 4
ggtttggtag aacaatctgc                                                    20

<210> SEQ ID NO 5
<211> LENGTH: 23
<212> TYPE: DNA
<213> ORGANISM: Artificial Sequence
<220> FEATURE:
<223> OTHER INFORMATION: Primer sequence Bhyo_12 F

<400> SEQUENCE: 5
```

```
cgtatgatta ttttacttgt cag                                          23

<210> SEQ ID NO 6
<211> LENGTH: 22
<212> TYPE: DNA
<213> ORGANISM: Artificial Sequence
<220> FEATURE:
<223> OTHER INFORMATION: Primer sequence Bhyo_12 R

<400> SEQUENCE: 6
ttttattaca gcaactttac tc                                           22

<210> SEQ ID NO 7
<211> LENGTH: 21
<212> TYPE: DNA
<213> ORGANISM: Artificial Sequence
<220> FEATURE:
<223> OTHER INFORMATION: Primer sequence Bhyo_17 F

<400> SEQUENCE: 7
tttttgccat aaatatctct c                                            21

<210> SEQ ID NO 8
<211> LENGTH: 19
<212> TYPE: DNA
<213> ORGANISM: Artificial Sequence
<220> FEATURE:
<223> OTHER INFORMATION: Primer sequence Bhyo_17 R

<400> SEQUENCE: 8
gaaatgccgt ccttcttag                                               19

<210> SEQ ID NO 9
<211> LENGTH: 24
<212> TYPE: DNA
<213> ORGANISM: Artificial Sequence
<220> FEATURE:
<223> OTHER INFORMATION: Primer sequence Bhyo_21 F

<400> SEQUENCE: 9
aaaataatga tgaagtatct aatg                                         24

<210> SEQ ID NO 10
<211> LENGTH: 22
<212> TYPE: DNA
<213> ORGANISM: Artificial Sequence
<220> FEATURE:
<223> OTHER INFORMATION: Primer sequence Bhyo_21 R

<400> SEQUENCE: 10
aagtatcagg taaaggtaaa tc                                           22

<210> SEQ ID NO 11
<211> LENGTH: 19
<212> TYPE: DNA
<213> ORGANISM: Artificial Sequence
<220> FEATURE:
<223> OTHER INFORMATION: Primer sequence Bhyo_22 F

<400> SEQUENCE: 11
agattaaaaa ctgacggag                                               19

<210> SEQ ID NO 12
<211> LENGTH: 19
<212> TYPE: DNA
```

```
<213> ORGANISM: Artificial Sequence
<220> FEATURE:
<223> OTHER INFORMATION: Primer sequence Bhyo_22 R

<400> SEQUENCE: 12
agcacaagaa ccttcaaac                                                    19

<210> SEQ ID NO 13
<211> LENGTH: 28
<212> TYPE: DNA
<213> ORGANISM: Artificial Sequence
<220> FEATURE:
<223> OTHER INFORMATION: Primer sequence Bhyo_10 F

<400> SEQUENCE: 13
ctctctttta tatttttat tatagttg                                           28

<210> SEQ ID NO 14
<211> LENGTH: 20
<212> TYPE: DNA
<213> ORGANISM: Artificial Sequence
<220> FEATURE:
<223> OTHER INFORMATION: Primer sequence Bhyo_10 R

<400> SEQUENCE: 14
ttgatgaaat tagaccattc                                                   20

<210> SEQ ID NO 15
<211> LENGTH: 28
<212> TYPE: DNA
<213> ORGANISM: Artificial Sequence
<220> FEATURE:
<223> OTHER INFORMATION: Primer sequence Bhyo_23 F

<400> SEQUENCE: 15
caccctttag acttattatt ttattttg                                          28

<210> SEQ ID NO 16
<211> LENGTH: 19
<212> TYPE: DNA
<213> ORGANISM: Artificial Sequence
<220> FEATURE:
<223> OTHER INFORMATION: Primer sequence Bhyo_23 R

<400> SEQUENCE: 16
ttgttctgcg tgcgtgtag                                                    19

<210> SEQ ID NO 17
<211> LENGTH: 775
<212> TYPE: DNA
<213> ORGANISM: Brachyspira hyodysenteriae
<220> FEATURE:
<221> NAME/KEY: misc_feature
<223> OTHER INFORMATION: TlyA (tlyA) gene, partial cds, GenBank:
      KU215622.1

<400> SEQUENCE: 17
gtaaatatga gagataaaga aagaaattct ctttctataa taaaatcttt ccttggatta        60
taatactaat ataaatgcga ttagatgaat atgtgcatag tgaaggctat acagaaagca       120
gatctaaagc acaggatata atactagccg gttgtgtttt tgttaatgga gtaaaggtaa       180
cttctaaggc tcataaaata aaagatactg ataatataga agttgttcag aatataaaat       240
atgtatcaag agctggagaa aaattagaaa aggcgtttgt agaatttgga atatctgtag       300
aaaataaaat atgtttagat ataggagctt ctacaggagg atttacagat tgtctgctta       360
```

```
agcatggtgc taaaaaagtt tatgctcttg atgtaggaca taatcagcta gtttataaac    420
ttcgtaatga taatagggta gtgtcaatag aagatttcaa tgccaaagat ataaataaag    480
aaatgttcaa tgatgaaatc ccatctgtaa tagtaagtga cgtatcattt atatcaataa    540 caaaatagc accaatcata tttaaagaat taaataattt agagttttgg gtaactttaa     600 taaaccaca atttgaagct gaaagaggtg atgtttcaaa aggcggtata atacgagatg     660
atatacttag agaaaaaata ttaaataatg ctatttcaaa gataatagac tgcggattta    720
aagaagttaa tagaaccatc tctcctataa aaggtgctaa aggtaatata gaata         775
```

<210> SEQ ID NO 18
<211> LENGTH: 20
<212> TYPE: DNA
<213> ORGANISM: Artificial Sequence
<220> FEATURE:
<223> OTHER INFORMATION: Bh tlyA_F primer

<400> SEQUENCE: 18

```
gcagatctaa agcacaggat                                                20
```

<210> SEQ ID NO 19
<211> LENGTH: 20
<212> TYPE: DNA
<213> ORGANISM: Artificial Sequence
<220> FEATURE:
<223> OTHER INFORMATION: Bh tlyA_R primer

<400> SEQUENCE: 19

```
gcctttgaa acatcacctc                                                 20
```

<210> SEQ ID NO 20
<211> LENGTH: 1346
<212> TYPE: DNA
<213> ORGANISM: Brachyspira pilosicoli
<220> FEATURE:
<221> NAME/KEY: misc_feature
<223> OTHER INFORMATION: gene for 16S ribosomal RNA, partial sequence

<400> SEQUENCE: 20

```
atgcagtcga gcgggcttat tcgggcaact ggataagtta gcggcgaact ggtgagtaac    60
acgtaggtaa tctgccgtga agtggggat aacccatgga aacatggact aataccgcat     120
atactcttgc tacataagta gagtagagga aagttttttc gcttcacgat gagcctgcgg    180
cctattagcc tgttggtagg gtaatggcct accaaagcta cgataggtag ccgacctgag    240
agggtgaccg gccacattgg gactgagata cggcccagac tcctacggga ggcagcagct    300
gagaatcttc cacaatggac gaaagtctga tggagcgaca tcgcgtgagg gatgaaggcc    360
ttcgggttgt aaacctcgga aattatcgaa gaatgagtga cagtagataa tgtaagcctc    420
ggctaactac gtgccagcag ccgcggtaat acgtaggagg caaacgttgc tcggatttac    480
tgggcgtaaa gggtgagtag gcggatttat aagtctaagg tgaaagaccg aagctcaact    540
tcgggaacgc tcggatact gtaagtcttg gatattgtag gggatgatgg aattctcggt    600
gtagcggtgg aatgcgcaga tatcgagagg aacacctata gcgaaggcag tcatctgggc    660
atttatcgac gctgaatcac gaaagctagg ggagcaaaca ggcttagata ccctggtagt    720
cctagccgta aacgttgtac actaggtgct ctatttaaa taggagtgcc gtagctaacg    780
tcttaagtgt accgcctgag gagtatgccc gcaagggtga aactcaaaga aattgacggg    840
tccccgcaca gtggtggag catgtggttt aattcgatga tacgcgaaaa accttacctg    900
```

```
                                    -continued ggtttgaatt gttagatgaa tgatttagag ataagtcaga ccgcaaggac gtttaacata        960
ggtgctgcat ggctgtcgtc agctcgtgtc gtgagatgtt gggttaagtc ccgcaacgag       1020
cgcaaccctc accctctgtt gctaacgagt aatgtcgagc actcttaggg gactgcctac       1080
gttcaagtag gaggaaggtg gggatgatgt caagtcctca tggcccttat gtccagggct       1140
acacacgtgc tacaatggca agtacaaaga gaagcaagac cgcgaggtgg agcaaaactc       1200
aaaaaagttg cctcagttcg gattggagtc tgaaactcga ctccatgaag ttggaatcac       1260
tagtaatcgt agatcagaac gctacggtga atacgttccc ggggattgta cacaccgccc       1320
gtcacgccat cggagttggt tttacc                                            1346

<210> SEQ ID NO 21
<211> LENGTH: 26
<212> TYPE: DNA
<213> ORGANISM: Artificial Sequence
<220> FEATURE:
<223> OTHER INFORMATION: Bp16S_ F: 5 primer

<400> SEQUENCE: 21
cataagtaga gtagaggaaa gttttt                                              26

<210> SEQ ID NO 22
<211> LENGTH: 24
<212> TYPE: DNA
<213> ORGANISM: Artificial Sequence
<220> FEATURE:
<223> OTHER INFORMATION: Bp16S_R: 5 primer

<400> SEQUENCE: 22
ctcgacatta ctcggtagca acag                                                24
```

SWINE DYSENTERY VACCINE

RELATED APPLICATIONS

This application is a continuation-in-part of U.S. patent application Ser. No. 14/900,246, filed on Dec. 21, 2015, now U.S. Pat. No. 9,855,322; which is a 35 U.S.C. § 371 national stage filing of International Patent Application No. PCT/EP2014/063695, filed on Jun. 27, 2014; which claims priority to European Patent Application No. 13382255.1, filed on Jun. 28, 2013. This application also claims priority to European Patent Application No. 17382711.4, filed on Oct. 24, 2017. The entire contents of each of the foregoing applications are incorporated herein by reference.

SEQUENCE LISTING

This application contains a Sequence Listing which has been submitted in ASCII format via EFS-Web and is hereby incorporated by reference in its entirety. Said ASCII copy, created on Dec. 28, 2017, is named 117814-36202_Sequence_Listing.txt and is 7,503 bytes in size.

TECHNICAL FIELD

The present invention relates to a composition comprising *Brachyspira hyodysenteriae* bacteria, e.g., a single strain of *Brachyspira hyodysenteriae* bacteria, particularly in the field of immunization against swine dysentery.

BACKGROUND ART

Swine dysentery (SD), caused by colonic infection with the spirochaete *Brachyspira hyodysenteriae*, remains a major problem worldwide. It affects swine mainly during the fattening period. *Brachyspira hyodysenteriae* is a Gram-negative, oxygen-tolerant, anaerobic spirochete that colonizes the porcine large intestine to cause swine dysentery (SD). This condition is characterized by a severe mucohemorrhagic diarrhoea that primarily affects animals during the growing-finishing period and has been reported from all major pig-rearing countries (Hidalgo, A. et al., *Journal of Clinical Microbiology* (2010), 48(8):2859-2865).

SD is a widely distributed disease around the world, although studies regarding epidemiology are scarce and the reported prevalence significantly varies among them. Thus, *B. hyodysenteriae* reported prevalence ranges from 0% to near 40%. Variations in prevalence can be due to the use of different diagnostic methods or to differences among countries in housing, management, feeding regimes, etc. Moreover, whereas in many countries the prevalence may be concealed by the use of antimicrobials as feed additives, in others the ban of antibiotics as growth promoters may have resulted in an increase in SD prevalence (Alvarez-Ordóñiez, A. et al., International Journal of Environmental Research and Public Health (2013), 10:1927-1947).

Carrier pigs play a main role in the epidemiology of swine dysentery and are considered the major source of transmission between herds. *B. hyodysenteriae* survives in the environment for long periods, especially in liquid faeces contained in pits and lagoons, where it may remain infective for up to 60 days. For instance, it can survive during several months in pig faeces at low temperatures. This spirochete also can naturally colonize mice, rheas, chickens, and mallards, and together with mechanical vectors or fomites, this increases the ways in which *B. hyodysenteriae* may be spread within and between herds (Hidalgo, A. et al., *Journal of Clinical Microbiology* (2010), 48(8):2859-2865).

The disease causes important direct financial losses, especially in intensive pig farms, derived from a decrease in food conversion efficiency, mortality, lengthening of the fattening period and also indirect losses, like an increase in veterinary expenses, medication, etc. The eradication of the disease through medication is quite difficult, since many clinically recovered animals keep shedding the organism for a long time while acting as carriers.

Treatment of SD involves the use of antibiotics. Pleuromutilins (tiamulin and valnemulin) have been used for this purpose in the European Union (EU). Tiamulin and valnemulin are semi-synthetic derivatives of the naturally occurring diterpene antibiotic pleuromutilin which show outstanding activity against anaerobic bacteria and are used exclusively in animals, largely in swine. Also macrolides (tylosin and, more recently, tylvalosin) and the closely related lincomycin (lincosamide) have been commonly included in SD therapeutic strategies. However, the emergence of *B. hyodysenteriae* strains with reduced susceptibility to one or more of these antibiotics and the presence of genetically diverse multiresistant isolates has been confirmed in several countries. This fact complicates treatment and control of SD and should alert veterinary surgeons and pig farmers for the need of a strategic approach to select antibiotics, which must only be used on strict indications following proper field and laboratory diagnosis in order to guarantee their long-term efficiency for SD treatment (Alvarez-Ordóñiez, A. et al., International Journal of Environmental Research and Public Health (2013), 10:1927-1947).

The high costs of medication, together with the fact that on many occasions it is impossible to eradicate the infection completely, and the increasing worries about the presence of drug residues in both meat products and the environment, justifies the development of efficient immunoprophylactic methods to control SD (Diego, R. et al., *Vaccine* (1995), 13(7):663-667).

Large efforts have been made in order to develop vaccines to control SD since Joens and co-authors (Joens, L. A., et al., *American Journal of Veterinary Research* (1979), 40:1352-1354) reported that pigs which have recovered from acute SD are protected from disease when subsequently re-exposed to *B. hyodysenteriae*, indicating that the infection can induce a protective immune response (Alvarez-Ordóñiez, A. et al., *International Journal of Environmental Research and Public Health* (2013), 10:1927-1947). However, attempts to develop vaccines to control SD have met with limited success. Hudson (Hudson, M. J. et al., *British Veterinary Journal* (1974), 130:37-40; Hudson, M. J. et al., *Research in Veterinary Science* (1976), 21:366-367) developed an attenuated live vaccine which was unable to protect against a subsequent challenge. Glock (Glock, R. D. et al., *Proceedings of the 6th International Pig Veterinary Society Congress* (1980), Copenhagen, Denmark, p. 521) reported some degree of protection upon challenge after six intravenous injections, at six-day intervals, of an inactivated vaccine. Attenuated or genetically modified live avirulent vaccines may show reduced colonization and cause less immune stimulation (Alvarez-Ordóñiez, A. et al., *International Journal of Environmental Research and Public Health* (2013), 10:1927-1947).

An alternative approach is to generate subunit vaccines that might be delivered by the expression of recombinant *B. hyodysenteriae* proteins on a bacterial delivery vector. Efforts have been made to identify *B. hyodysenteriae* proteins for use in subunit vaccines, but vaccination with a recombinant 38 kDa flagellar protein failed to prevent colonization in experimentally infected pigs (Gabe et al., Infection and Immunity (1995), 63:142-148). On the other hand, vaccination with a recombinant 29.7 kDa outer membrane lipoprotein (Bhlp29.7) resulted in partial protection, with fewer animals developing disease than occurred in the control groups. The authors of this study concluded that vaccination also tended to delay the onset of faecal shedding of spirochaetes, but did not necessarily stop it from occurring (La, T. et al., *Veterinary Microbiology* (2004), 102:97-109). On a study conducted by Holden et al., the efficacy of vaccination with smpB (an outer membrane protein of *B. hyodysenteriae*) was evaluated. However, the response induced after protein vaccination offered only moderate protection against the disease (Holden, J. et al., *Veterinary Microbiology* (2008), 128:354-363). In most occasions recombinant vaccines tested have failed to provide enough protection in pigs (Alvarez-Ordóñiez, A. et al., *International Journal of Environmental Research and Public Health* (2013), 10:1927-1947).

Vaccines consisting of whole cell bacterins induce serum antibody responses to *Brachyspira hyodysenteriae*, yet generally fail to protect pigs from disease. The use of *B. hyodysenteriae* bacterins prepared from whole cell lysates may even exacerbate disease upon infection (Waters, W. R. et al., Vaccine (2000), 18:711-719). Moreover, bacterin vaccines tend to be lipopolysaccharide serogroup-specific, which then requires the use of autogenous bacterins. Furthermore, *B. hyodysenteriae* bacterins are relatively difficult and costly to produce on large scale because of the fastidious growth requirements of the anaerobic spirochaete (La, T. et al., Veterinary Microbiology (2004), 102:97-109). In some countries, bacterin vaccines for SD are available commercially, and provide a degree of protection. However, as stated above, they tend to be lipooligosaccharide (LOS) serogroup specific, which then requires the use of autogenous or multivalent preparations (Hampson, D. J. et al., *Diseases of Swine* (2006), 10$^{th}$ Edition, Blackwell Publishing Professional, Ames, Iowa, U.S.A., pp. 687-688). Other references to SD vaccines in the art can be found in the following patent literature:

U.S. Pat. No. 4,748,019: The authors found that an effective regime of vaccination comprises administering parenterally to pigs a priming dose of killed virulent or pathogenic *T. hyodysenteriae* effective to stimulate the immune response of the pig (strain "P18A", NCTC 11615) to a subsequent dose of a live avirulent or non-pathogenic strain of *T. hyodysenteriae* (strain "VSI", NCTC 11628) and at about the same time or thereafter administering this live strain orally.

U.S. Pat. No. 5,750,118: The invention relates to a vaccine against SD comprising an effective quantity of inactivated and adjuvant-containing *T. hyodysenteriae* antigen (virulent or attenuated strain) for intradermal administration. The vaccine antigen is prepared from the strain No. 27164 ATCC, which is inactivated.

U.S. Pat. No. 5,281,416: The invention relates to a method of vaccination of a pig against SD characterized by parenteral, preferably intramuscular administration to the pig of a live strain or of an oxygen-treated non-viable strain of *T. hyodysenteriae*. Representative strains which may be used are reference virulent strains ATCC 31287, ATCC 31212 and the reference avirulent strain ATCC 27164.

EP 3013363: The application relates to compositions and vaccines comprising combinations of different genetically diverse strains of *B. hyodysenteriae*. Further identified in the application are strains CNCM I-4720, CNCM I-4721 and CNCM I-4722.

However, the efficacy of these vaccines was found to be variable. In some cases, when different strains are used as ingredients of a vaccine, it can be difficult to put into practice with regard to regulatory constraints. For example, according to European regulation, each active substance in a veterinary medicine composition must be both perfectly identified and quantified in the active substance. Therefore, if a composition comprises several strains, it can be necessary to develop tests that are able to both identify and quantify each strain individually. Such tests can be very difficult to develop from a technical point of view. Autogenous preparations (also known as "autovaccines", which may be defined as vaccines prepared from cultures of organisms isolated from the diseased animal's own tissues or secretions) have been used to further improve some of these vaccines. This approach, albeit efficient, is highly cost and time expensive and confers protection only for a single strain of *B. hyodysenteriae*. Moreover, the vaccination occurs sometime after the strain causing the disease has been identified, which can take several weeks (for instance, under standard procedures, the isolation process from the samples from the farm, initial culture and autovaccine production may take at least 6 weeks). This delay in time often causes the propagation of the bacteria in other animals from the herd, or in extreme circumstances, even to other pig farms. It also provokes serious economic losses and it is itself an expensive procedure to be applied on routine basis. SD thus remains an important endemic infectious disease in many pig rearing countries. There is a huge necessity of an effective and economically affordable vaccine for SD, e.g., a single strain based vaccine for CD.

SUMMARY OF THE INVENTION

Swine Dysentery (SD) is a severe mucohaemorhagic enteric disease of pigs caused by *Brachyspira hyodysenteriae*, which has a large impact on pig production and causes important losses due to mortality and sub-optimal performance Considering the emergence of multi-resistant strains and the concern that drug residues may be present in meat products or the environment, efficient immunoprophylactic methods to control SD are urgently needed. However, the available vaccines, e.g., single strain vaccines, fail to confer a satisfactory degree of protection against infection and, even if they confer a certain degree of protection, they do not provide adequate cross-protective immunity against strains of different MLVA types, clonal complexes and/or serogroups. Moreover, the fabrication and commercialization of autovaccines present many inconveniences. Finally, it should be noted that compositions that comprise a combination of multiple strains may be subject to technical and regulatory constraints. Accordingly, there is a necessity of vaccines against SD which confer strong protection against strains of different serogroups, namely an effective and universal SD vaccine. There is also a necessity of vaccines against SD which are based on a single strain and which nevertheless confer protection against different strains, namely an effective single strain based SD vaccine.

The inventors have developed a vaccine against SD that, unexpectedly, is as efficient as an autovaccine, despite not having in its composition the strain which causes the infection. This effect is highly surprising, as it is in conflict with the autovaccine theory. This invention provides a vaccine with efficient and general protection against *Brachyspira hyodysenteriae*, namely a "universal vaccine".

The inventors have also developed an effective vaccine against SD based on a single strain that provides protection against SD, and demonstrated the effects with a challenge with the strain B204, a reference strain for the evaluation of vaccines against SD. This strain is deposited in the American Type Culture Collection (ATCC) as ATCC 31212 and publically available. The strain is herein also referred to as the challenge strain. This strain B204 is not particularly closely related to the strain of the present invention (see FIG. 1: CNCM I-4720 is MLVA type 3, B-204 is MLVA type 23). This effect is therefore highly surprising, as it is in conflict with the autovaccine theory as well as the theory that multiple diverse strains would be necessary to grant a broader protection against different *Brachyspira hyodysenteriae* strains. This protection against a distant strain shows that the protection granted by the vaccine of the present invention is not limited to closely related strains, as e.g., autovaccines, but confers a broad protection against different *Brachyspira hyodysenteriae* strains. Such a protection, which is not limited to strains that are closely related to the strain used as a vaccine, but instead confers protection also against distant strains of e.g., different clonal complexes, is herein referred to as a universal protection, and the vaccine is accordingly referred to as a universal vaccine.

In a first aspect, the present invention provides a composition comprising bacteria from at least two genetically diverse strains of *Brachyspira hyodysenteriae*. The composition of the invention may comprise inactivated strains and the genetic diversity may be conferred by selecting the at least two genetically diverse strains of *Brachyspira hyodysenteriae* from different clonal complexes. In a preferred aspect, the genetically diverse strains are at least detected in a proportion of 1% with respect to the total of detected strains in a region of interest. The region of interest may be any region, preferably Spain.

In a second aspect, the present invention is related to the composition of the invention for its use as a vaccine, preferably a vaccine against swine dysentery caused by *Brachyspira hyodysenteriae*.

Moreover, the invention provides a method for producing the composition of the invention, comprising selecting at least two genetically different strains and mixing them in equal quantity to achieve a concentration of at least between $10^8$ and $10^9$ bacteria/mL.

In a third aspect, the present invention provides a composition comprising bacteria from a single strain of *Brachyspira hyodysenteriae*, wherein said strain is the strain that has been deposited by the applicant at the *Collection Nationale de Cultures de Microorganismes* (CNCM), Institut Pasteur, 28, Rue du Docteur Roux, 75724 Paris Cédex 15, France, on Mar. 14, 2013, with registration number CNCM I-4720 (hereinafter also referred to as strain CNCM I-4720 or strain H57 or the strain of the present invention).

In a fourth aspect, the present invention is related to the composition of the invention for its use as a vaccine, preferably a vaccine against swine dysentery caused by *Brachyspira hyodysenteriae*. Moreover, the invention provides a method for producing the composition of the invention, at a concentration of at least between $10^8$ and $10^9$ bacteria/mL.

In a fifth aspect, the present invention provides methods for the prevention and/or treatment of diarrhea, for example mucous and/or bloody diarrhea, and swine dysentery, using any of the compositions and/or vaccines described herein.

The invention provides:

A composition for use in the prevention and/or treatment of swine dysentery, said composition comprising a single strain of *Brachyspira hyodysenteriae*, wherein no other *Brachyspira hyodysenteriae* strain is present in the composition, and wherein said strain is the strain with the deposit number CNCM I-4720.

A composition for use in a method of reducing the occurrence of mucous and/or bloody diarrhea, said composition comprising a single strain of *Brachyspira hyodysenteriae*, wherein no other *Brachyspira hyodysenteriae* strain is present in the composition, and wherein said strain is the strain with the deposit number CNCM I-4720.

A composition for use in a method of delaying the appearance of clinical signs and/or reducing the overall severity of diarrhea and/or swine dysentery, said composition comprising a single strain of *Brachyspira hyodysenteriae*, wherein no other *Brachyspira hyodysenteriae* strain is present in the composition, and wherein said strain is the strain with the deposit number CNCM I-4720.

A composition for use in a method of preventing and/or reducing the time of shedding of bacteria, said composition comprising a single strain of *Brachyspira hyodysenteriae*, wherein no other *Brachyspira hyodysenteriae* strain is present in the composition, and wherein said strain is the strain with the deposit number CNCM I-4720, wherein optionally the bacteria which shedding is prevented and/or reduced are *Brachyspira hyodysenteriae*.

The composition for use according to any of the preceding items, wherein the diarrhea and/or swine dysentery is caused by *Brachyspira hyodysenteriae*.

The composition for use according to any of the preceding items, wherein said composition is effective against an infection with *Brachyspira hyodysenteriae* which is of another clonal complex and/or another MLVA type than the strain of the composition.

The composition for use according to any of the preceding items, wherein the bacteria are inactivated.

The composition for use according to any of the preceding items, wherein the bacteria are present in a concentration of at least between $10^8$ and $10^9$ of total bacteria/mL, of between $10^8$ and $10^9$ of total bacteria/mL, or in a concentration of $5*10^8$ total bacteria/ml, and/or wherein the administered dosage is between 1 mL to 5 mL, optionally 2 mL, and/or wherein the bacteria are present in an amount of between $10^7$ and $10^{11}$ of total bacteria/dose, between $10^8$ and $10^{10}$ of total bacteria/dose, or in an amount of $10^9$ of total bacteria/dose.

The composition for use according to any of the preceding items, wherein the composition is administered by parenteral administration, preferably by intramuscular administration.

The composition for use according to any of the preceding items, wherein the prevention or treatment is a prevention or treatment of a pig, preferably of a domestic pig.

A vaccine comprising any of the above mentioned compositions.

A method of treating and/or preventing and/or reducing the occurrence of and/or delaying the appearance of clinical signs and/or reducing the overall severity of diarrhea in an animal using any of the compositions and/or vaccines of one or more of the previous items, wherein optionally said diarrhea is mucous and/or bloody diarrhea.

A method of treating and/or preventing and/or delaying the appearance of clinical signs and/or reducing the overall severity of swine dysentery in an animal using any of the compositions and/or vaccines of one or more of the previous items.

A method of preventing and/or reducing the time of shedding of *Brachyspira hyodysenteriae* in an animal using any of the compositions and/or vaccines of one or more of the previous items.

A method of helping to develop diarrhea and/or swine dysentery only at later stages and/or resolving diarrhea and/or swine dysentery sooner when compared to non-vaccinated animals and/or animals vaccinated with a low-dose vaccine in an animal using any of the compositions and/or vaccines of one or more of the previous items.

DETAILED DESCRIPTION OF THE INVENTION

Methods of the Invention

Figure 1:
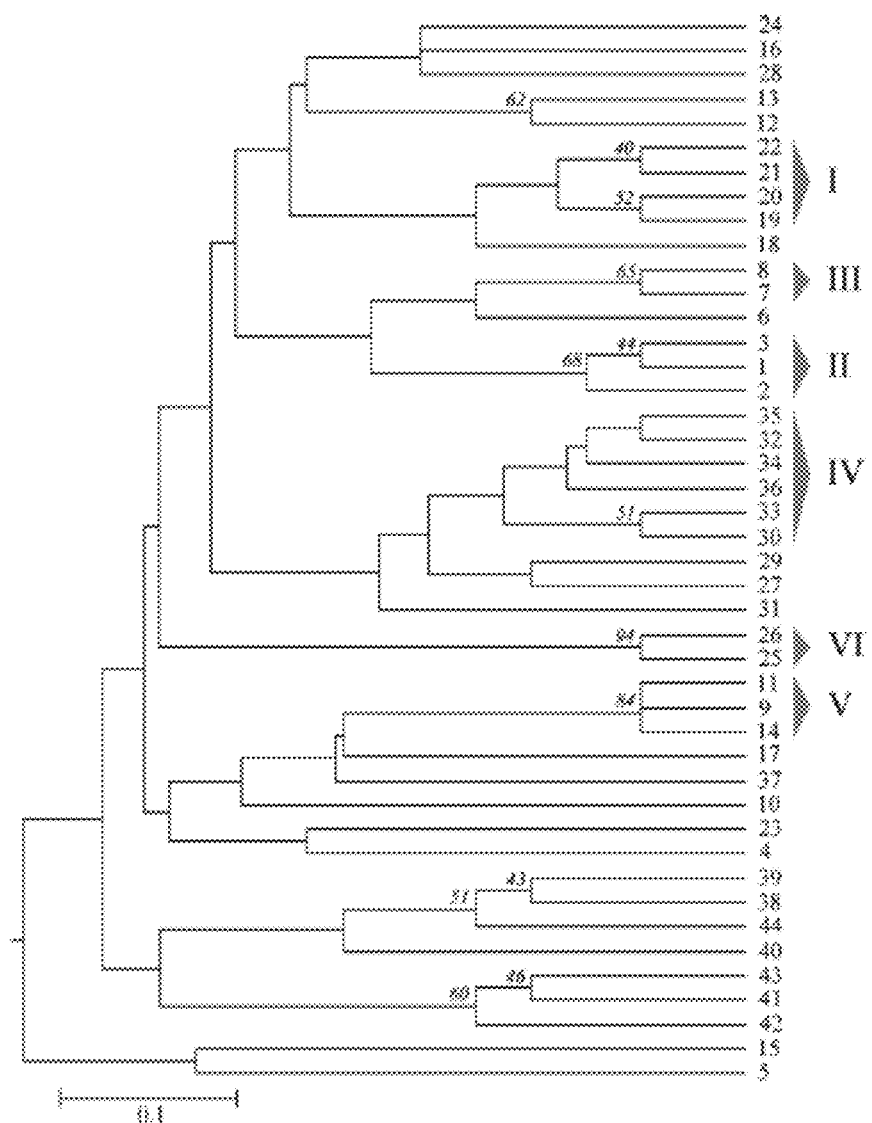
FIG. 1. Dendrogram of the 44 *B. hyodysenteriae* MLVA types found in the present study and clustered using UPGMA. Roman numerals I to VI indicate clonal complexes defined at the single-locus variant level. The scale bar represents genetic distance as the absolute number of differences in marker alleles among genotypes. Bootstrap values of >40% are shown. CNCM I-4720 is MLVA type 3, B-204 is MLVA type 23.

In the present invention, statements relating to compositions and/or vaccines have to be understood to also refer to methods and methods of treatment using said compositions and/or vaccines. In the present invention, statements relating to compositions and/or vaccines for use in a specific method, e.g., a method of treatment, have to be understood to also comprise an explicit disclosure of said method, e.g., the method of treatment.

For example, the present invention refers to methods of prevention or treatment of diarrhea, for example mucous and/or bloody diarrhea, and swine dysentery, using any of the compositions and/or vaccines described herein.

Composition of the Invention

The present invention relates to a composition comprising bacteria from at least two genetically diverse strains of *Brachyspira hyodysenteriae*. The term "genetically diverse" as used in the present invention refers to a defined set of genetic, measurable diverse characteristics in the genetic makeup of a species. To determine the diversity of microorganisms in defined environments (ecosystems) or to identify the spread of particular strains between hosts, genetic typing techniques which have the ability to distinguish diverse organisms of the same species are deployed. Importantly, when one is comparing the diversity of a single species between different ecosystems a robust statistical approach that allows an objective assessment is required. To this end, indices of diversity have been defined mathematically that are based on the frequency with which organisms of a particular type occur in a population or can be discriminated by a given typing tool (Grundmann, H. et al., *Journal of Clinical Microbiology* (2001), 39:4190-4192).

The present invention also relates to a composition comprising bacteria of strain CNCM I-4720. As demonstrated herein, such a composition can be used as an effective vaccine for the prevention or treatment of SD caused by distant strains.

A relatively high diversity among *B. hyodysenteriae* isolates has been classically described. The ability to understand the epidemiology of SD and to progress to its control depends on the availability of reliable strain typing methods to characterize the isolates. Based on the analysis of semi-purified lipopolysaccharides (LPS), four different serotypes were identified by Baum & Joens (Baum, D. H. et al., Infection and immunity (1979), 25:792-796), although further studies finally differentiated a total of 11 serogroups that included several serotypes (Hampson, D. J. et al., *Epidemiology and Infection* (1989), 102:75-84; Hampson, D. J. et al., *Epidemiology and Infection* (1990), 105:79-85; Hampson, D. J. et al., Swine dysentery. In: Intestinal Spirochaetes in Domestic Animals and Humans, pp. 175-209, edited by D. J. Hampson & T. B. Stanton. Wallingford: CAB International, 1997).

Differences in the geographical distribution of *B. hyodysenteriae* were demonstrated soon after. Reference strains from USA were classified within serotypes 1 and 2 while a higher variability regarding serotype classification was described for isolates from Europe and Australia (Harris et al., Swine Dysentery. In: Straw, B. E., D'Allaire, S. D., Mengeling, W. D. & Taylor, D. J. (Eds.) Disease of Swine. Iowa State University Press (1999), Ames Iowa USA, pp. 579-600). However, there is almost no recent information regarding serotype distribution of *B. hyodysenteriae* isolates. As a consequence of cross reactions, the techniques required to determine the serotype are slow and cumbersome to perform and give inconclusive results in a very high number of the isolates. For that reason, these techniques have been replaced by several molecular methods.

Different typing tools have been developed to discriminate between *B. hyodysenteriae* field isolates and provide a better understanding of the molecular epidemiology of the pathogen. Among them, a useful tool for strain typing of pathogenic microorganisms that has been introduced during the last few years is the multi-locus variable-number tandem-repeat analysis or MLVA. It has been developed as an important epidemiologic tool for strain typing of pathogenic microorganisms. MLVA is based on the PCR amplification of a number of well-selected and characterized loci that contain short repeat sequences (multiple loci of minisatellites called variable numbers of tandem repeats (VNTRs)). This sort of minisatellite consists of unique direct head-to-tail DNA repeats which can be found in all bacterial genomes and can be used to define specific isolates of bacterial species. In addition, VNTRs have been used to infer the bacterial population structure and phylogeny of diverse bacteria species. Within each repeat sequence locus the number of repeat copies can vary between different strains. By measuring the size of each PCR amplified loci, the number of repeat units can be deduced. Hidalgo and colleagues developed and tested a multiple-locus variable-number tandem-repeat analysis (MLVA) method that could be used in basic veterinary diagnostic microbiology laboratories equipped with PCR technology or in more advanced laboratories with access to capillary electrophoresis. Based on eight loci, and when performed on isolates from different farms in different countries, as well as type and reference strains, the developed MLVA technique was highly discriminatory (Hunter and Gaston discriminatory index, 0.938 [95% confidence interval, 0.9175 to 0.9584]) while retaining a high phylogenetic value. Using the technique, the species was shown to be diverse (44 MLVA types from 172 isolates and strains), although isolates were stable in herds over time. The population structure appeared to be clonal. The finding of *B. hyodysenteriae* MLVA type 3 in piggeries in three European countries, as well as other, related, strains in different countries, suggests that spreading of the pathogen via carrier pigs is likely. MLVA overcomes drawbacks associated with previous typing techniques for *B. hyodysenteriae* and is a powerful method for epidemiologic and population structure studies on this important pathogenic spirochete (Hidalgo, A. et al., *Journal of Clinical Microbiology* (2010), 48(8):2859-2865).

The inventors and their collaborators have applied this method on an international collection of *B. hyodysenteriae* isolates, including 115 Spanish field isolates as well as reference strains and isolates from Australia, Canada, E.E.U.U., UK and The Netherlands.

MLVA analysis reveals that Spanish field isolates of *B. hyodysenteriae* are heterogeneous and that the population has a clonal structure. A total number of 15 MLVA types were identified among Spanish isolates. Moreover, isolates with the same MLVA type were identified in Spain, UK and The Netherlands. On the other hand, it was concluded that isolates from Australia or EEUU have no common MLVA with Spanish isolates.

Figure 2:
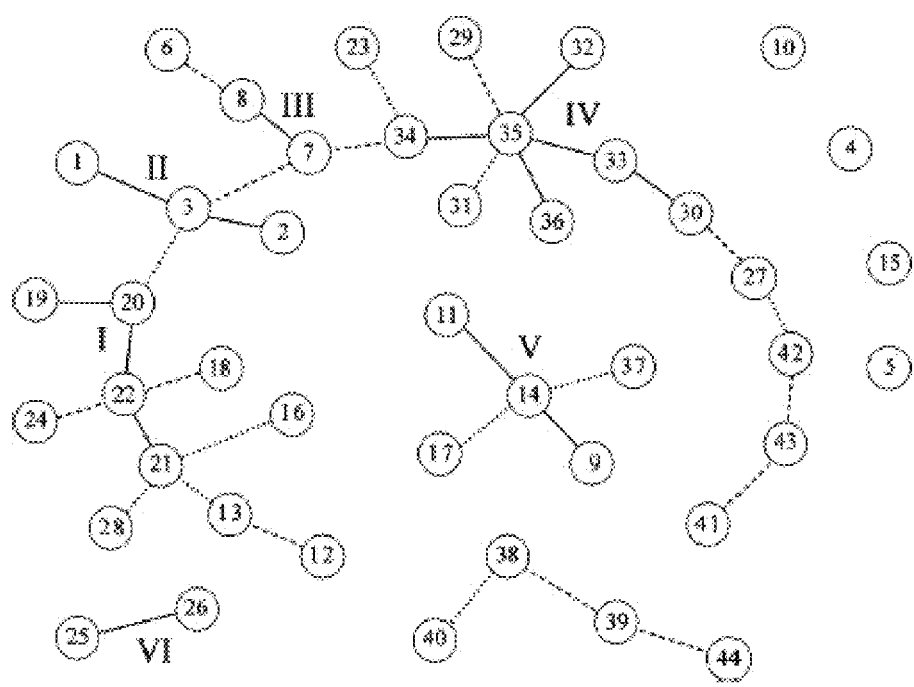
FIG. 2. MLVA types (circled) and relationships found among them according to the goeBURST algorithm. Solid lines show the single locus variant level, dashed lines show the double-locus variant level, and dotted lines show the triple-locus variant level. Groups at the single-locus variant level are indicated by roman numerals I to VI.

By grouping MLVA types at the single-locus variant level, a total number of six clonal complexes (I to VI) were established (FIG. 2).

The composition of the invention may comprise two, or three, or four, or five, or more genetically diverse strains. Preferably, the genetic diversity of the strains of the composition of the invention is conferred by selecting the at least two genetically diverse strains of *Brachyspira hyodysenteriae* from different clonal complexes. "Clonal complex" as used in the present invention refers to the several groups established by grouping the MLVA types at the single-locus variant level, as described above. More preferably at least one strain belongs to clonal complex II, and/or at least one strain belongs to clonal complex V, and/or at least one strain belongs to clonal complex I.

In the composition of the present invention, the genetically diverse strains preferably belong to the ancestral type from the clonal complex.

The common ancestor within each clonal complex was predicted using the goeBUST algorithm available at hypertext transfer protocol://goeburst.phyloviz.net/#Software, a global implementation of the eBURST algorithm. For more details see publications Feil et al., 2004 and Francisco et al., 2009, free at hypertext transfer protocol://goeburst.phyloviz.net/#Publications.

The composition of the present invention may further comprise a strain which belongs to a third clonal complex. Preferably, the third clonal complex is selected from the group consisting of clonal complex I, clonal complex II and clonal complex V.

Accordingly, the composition of the present invention comprises at least two, preferably three, genetically diverse strains of *Brachyspira hyodysenteriae*, wherein at least one of the strains belong to clonal complex I, and/or at least one of the strains belong to clonal complex II and/or at least one of the strains belong to clonal complex V.

Preferably, the composition of the invention comprises three genetically diverse strains of *Brachyspira hyodysenteriae* wherein one of the strains belong to clonal complex I, one of the strains belong to clonal complex II and one of the strains belong to clonal complex V.

Preferably, in the composition of the present invention at least one of the strains is the strain deposited within the *Collection Nationale de Cultures de Microorganismes* (CNCM), Institut Pasteur, on Mar. 14, 2013, with registration number CNCM I-4720, at least one of the strains is the strain deposited on the same date within the CNCM with registration number CNCM I-4721 and/or at least one of the strains is the strain deposited on the same date within the CNCM with registration number CNCM I-4722.

Accordingly, the present invention also provides the strains deposited within the *Collection Nationale de Cultures de Microorganismes* (CNCM), Institut Pasteur, on Mar. 14, 2013, with registration numbers CNCM I-4720, CNCM I-4721 and CNCM I-4722.

The strain with registration number CNCM I-4720 belongs to clonal complex II. The strain with registration number CNCM I-4721 belongs to clonal complex V. The strain with registration number CNCM I-4722 belongs to clonal complex I.

The present invention provides the strain with registration number CNCM I-4720 deposited within the Collection Nationale de Cultures de Microorganismes (CNCM), Institut Pasteur, on Mar. 14, 2013. The strain with registration number CNCM I-4720 belongs to clonal complex II, more specifically to the ancestral type of clonal complex II. The present inventors surprisingly found that a vaccine based on this strain is able to confer protection against a reference strain of another MLVA type which does not even belong to clonal complex II. Said single strain vaccine therefore confers a protection not only against strains from a single MLVA type, but also against more distant strains that are of a different MLVA type or do not even belong to the same clonal complex.

In some of the embodiments, the compositions disclosed herein comprise no other bacterial strain than strain CNCM I-4720. In some of the embodiments, the single strain composition of the present invention can be used in a method of preventing and/or treating swine dysentery, and/or in a method of reducing the occurrence of mucous and/or bloody diarrhea, and/or in a method of delaying the appearance of clinical signs, and/or in a method of reducing the overall severity of diarrhea and/or severe diarrhea, and/or in a method of preventing and/or reducing the time of shedding of *Brachyspira hyodysenteriae*, and/or in a method of helping to develop diarrhea only at later stages and/or resolving diarrhea sooner when compared to non-vaccinated animals and/or animals vaccinated with a low-dose vaccine. Preferably, the single strain composition of the present invention can be used in the prevention and/or treatment of swine dysentery. In some of the embodiments, the single strain composition of the present invention is effective in the prevention and/or treatment of swine dysentery caused by *B. hyodysenteriae* strains that are heterologous (compared to strain CNCM I-4720). In some of the embodiments, the single strain composition of the present invention is effective in the prevention and/or treatment of swine dysentery caused by *B. hyodysenteriae* strains that are of another clonal complex and/or another MLVA type and/or of a different serogroup than the strain CNCM I-4720. In some of the embodiments, the single strain composition of the present invention is effective in the prevention and/or treatment of swine dysentery caused by *B. hyodysenteriae* strains that are of the same clonal complex and/or MLVA type and/or serogroup than the strain CNCM I-4720. In some of the embodiments, the single strain composition of the present invention provides protection against different strains of different serogroups. In some of the embodiments, the single strain composition of the present invention represents an effective and universal single strain based SD vaccine.

In the composition of the present invention the genetically diverse strains are preferably epidemiologically relevant. In the context of the present invention, "epidemiologically relevant" means that the strains are at least detected in a proportion of 1-100%, preferably at least 1%, at least 2%, at least 3%, at least 4%, at least 5%, at least 10%, at least 15%, at least 20%, at least 25%, at least 30%, at least 50%, at least 75%, at least 90% or 100% with respect to the total of detected strains in a region of interest. Preferably, the genetically diverse strains are at least 1% detected with respect to the total of detected strains in a region of interest. In the context of the present invention, "detected" means that said strains were identified in the region of interest. The detection of the bacteria *Brachyspira hyodysenteriae* can be done e.g. in rectal swabs, colonic mucosa and/or faecal samples from pigs. For example, the samples can be cultured and the DNA can be extracted following previously reported methods (see e.g. Hidalgo, A. et al., Journal of Clinical Microbiology (2010), 48(8):2859-2865). The presence of *B. hyodysenteriae* can be detected by PCR methods. The presence of *B. hyodysenteriae* can be also confirmed by streaking bacteriology swabs taken from faeces or the colonic walls of pigs onto selective agar plates. After incubation of the plates in anaerobic environment, the presence of low flat spreading growth of spirochaetes on the plate, and hemolysis around the growth can be recorded (La, T. et al., Veterinary Microbiology (2004), 102:97-109). Alternatively, the presence of *B. hyodysenteriae* can be performed by suspending the samples in PBS and detecting the presence of the bacteria with an indirect immunofluorescence test (IFT) (see e.g. Diego, R. et al., Vaccine (1995), 13(7):663-667). Other methods of detecting the presence of *B. hyodysenteriae* known in the art can be employed.

The term "region of interest" as employed in the present invention refers to a demarcated area of the Earth, i.e. to a geographical region or a geographical area wherein the presence of *B. hyodysenteriae* is assessed. There is no specific limitation to the geographical region of interest. It can vary from thousands of kilometers at continental level to a few kilometers at local level. For example, the region of interest can be part of a country, a whole country or more than one country. Preferably, the region of interest is a country or a group of countries. For example, the region of interest can be Europe. Preferably, the region of interest can be Spain, more preferably Iberian Peninsula Spanish territory, in particular Castilla y León, Andalucía and/or Extremadura. Other preferred regions of interest are Italy, The Netherlands, United Kingdom, Australia, Canada and/or United States.

Moreover, the bacteria comprising the composition of the present invention may be inactivated, i.e., they may be chemically or physically inactivated. The inactivation comprises killing the bacteria with chemicals, heat, and/or radiation. The bacteria of the composition can be inactivated by any inactivation procedure known in the art. Preferably, the bacteria of the composition of the invention are inactivated by treating the bacteria with formaldehyde. Most preferably, the formaldehyde is injected in to the bacteria culture at 0.5% and it is then incubated overnight (18 hours, approx.) at 37° C. with light agitation.

According to the present invention, the bacteria of the composition, which are preferably inactivated, may be present in a concentration of at least between $10^7$ and $10^{12}$ bacteria/mL, preferably in a concentration of at least $10^7$, or $10^8$, or $5.10^8$, or $10^9$, or $10^{10}$, or $10^{11}$ or $10^{12}$ bacteria/mL, preferably in a concentration of between $10^8$ and $10^{10}$ bacteria/mL, more preferably in a concentration of between $10^8$ and $10^9$ bacteria/mL, even more preferably in a concentration of $5.10^8$ bacteria/mL. In accordance with some embodiments of the invention, these numbers may refer to bacterial from a single strain of *B. hyodysenteriae*.

If the composition comprises bacteria belonging to two strains, they may be present in the composition in a ratio of 1:(0.5-2). If the composition comprises bacteria belonging to three strains, they may be present in the composition in a ratio of 1:(0.5-2):(0.5-2). If the composition comprises bacteria belonging to four strains, they may be present in the composition in a ratio of 1:(0.5-2):(0.5-2):(0.5-2). If the composition comprises bacteria belonging to five strains, they may be present in the composition in a ratio of 1:(0.5-2):(0.5-2):(0.5-2):(0.5-2). Preferably, the composition comprises bacteria in an equal mixture of the selected strains, namely in a ratio of 1:1, 1:1:1, 1:1:1:1, 1:1:1:1:1, depending on how many different strains the composition comprises. In this context, "ratio" means number of bacteria/mL.

The concentration of bacteria in the composition can be calculated using any method known in the art. For example, Neubauer chamber counting can be used to estimate the number of bacteria present in the composition of the invention. This method can also be applied to inactivated bacteria.

The composition of the present invention comprises preferably a total amount of $10^8$ to $10^9$ inactivated bacteria/mL in an equal mixture of the selected strains, wherein the bacteria belong to three genetically diverse strains of *Brachyspira hyodysenteriae*, wherein one of the strains belong to clonal complex I, one of the strains belong to clonal complex II and one of the strains belong to clonal complex V, and wherein preferably the genetically diverse strains are epidemiologically relevant in a region of interest, i.e. are present in Spain in at least a proportion of 1% with respect to the total of detected strains.

Preferably, the genetically diverse strains that are epidemiologically relevant in a region of interest are each present in a proportion of at least 9% with respect to the total of detected strains. Preferably, one of the strains is present in a proportion of at least 13% with respect to the total of detected strains. More preferably two of the strains are present in a proportion of at least 13% with respect to the total of detected strains. Most preferably, one of the strains is present in a proportion of at least 24% with respect to the total of detected strains.

The composition of the present invention may further comprise an adjuvant. An adjuvant is a component that potentiates the immune response to an antigen and/or modulates it towards the desired immune responses. It may be an inorganic or organic chemical, macromolecule or whole cells of certain killed bacteria which enhances the immune response to given antigen. In the context of the present invention, the adjuvant that may be present in the composition of the invention can be any suitable adjuvant which e.g. enhances, accelerates and prolongs the specific immune response as known in the current art.

Adjuvants may include for instance:
Mineral salts, e.g., aluminium hydroxide and aluminium or calcium phosphate gels.
Oil emulsions and surfactant based formulations, e.g., MF59 (microfluidised detergent stabilised oil-in-water emulsion), QS21 (purified saponin), AS02 [SBAS2] (oil-in-water emulsion+MPL+QS-21), Montanide™ ISA-51, ISA-720, IMS (stabilised water-in-oil emulsion).
Particulate adjuvants, e.g., virosomes (unilamellar liposomal vehicles incorporating influenza haemagglutinin), AS04 ([SBAS4] A1 salt with MPL), ISCOMS (structured complex of saponins and lipids), polylactide co-glycolide (PLG).
Microbial derivatives (natural and synthetic), e.g., monophosphoryl lipid A (MPL), Detox (MPL+M. Phlei cell wall skeleton), AGP [RC-529] (synthetic acylated monosaccharide), DC_Chol (lipoidal immunostimulators able to self organise into liposomes), OM-174 (lipid A derivative), CpG motifs (synthetic oligonucleotides containing immunostimulatory CpG motifs), modified LT and CT (genetically modified bacterial toxins to provide non-toxic adjuvant effects).

Endogenous human immunomodulators, e.g., hGM-CSF or hIL-12 (cytokines that can be administered either as protein or plasmid encoded), Immudaptin (C3d tandem array)

Inert vehicles, such as gold particles towards the desired response to vaccine antigens.

The most preferred adjuvants are aluminum salts (aluminum hydroxide or aluminum phosphate) and mineral oils. When inoculated they produce a small granuloma that allows the delayed liberation of the antigen (long lasting antigenic stimulation) and the attraction of antigen-presenting cells. This increases the immune response. For example, the adjuvant may be HAVLOGEN™ or Montanide™. Most preferably, the adjuvant may be a commercial oil adjuvant such as Montanide™ IMS 251 C VG (SEPPIC).

The adjuvant is preferably present in the final composition in a concentration in the final formula of 5 to 50% vol/vol respect to final injection volume, preferably 5%, 10%, 20%, 25%, 30%, 40%, 50% or more (vol/vol, i.e. volume with respect to final injection volume). More preferably, the concentration of adjuvant in the final formula is 20% vol/vol (i.e. volume with respect to final injection volume).

The composition of the invention may additionally comprise other components. For example, the composition may comprise antiseptic and/or antifungal agents. For example, the composition may further comprise Thimerosal (Sigma), also known as Thiomersal. In some embodiments, Thimerosal is comprised in an amount of 0.005 to 1 g per 100 ml, preferably in an amount of 0.5, or 0.3 or 0.1, or 0.05, or 0.03, or 0.02, or 0.01 or 0,005 g per 100 ml. In some embodiments, thimerosal is comprised in an amount of 0.01 g per 100 ml. In a particularly preferred embodiment, the composition does not comprise Thimerosal. In an even more preferred embodiment, the composition does not comprise any mercurial derivatives. In a most preferred embodiment, the composition does not comprise any heavy metals and/or preserving agents.

Further, the composition of the invention may also comprise buffer solutions such as salts. Preferably, the composition of the invention may comprise a buffer in a concentration of 0.01 to 0.5 M, preferably in a concentration of 0.5M, or 0.4M, or 0.3M, or 0.2M, or 0.1M, or 0.05M, or 0.01M. The buffer may be any suitable buffer described in the art. For example, the buffer may be phosphate buffered saline (PBS) or sodium acetate. Preferably, the buffer is sodium acetate 0.1M.

Vaccine of the Invention

The composition of the present invention may be preferably used as a vaccine. A vaccine is a biological preparation that improves immunity to a particular disease. According to the present invention, the vaccine is preferably a vaccine against swine dysentery (SD). Preferably, the swine dysentery is caused by *Brachyspira hyodysenteriae*.

The composition of the invention for use as a vaccine (from now on, the vaccine of the invention) may be suitable for administration to swine in a particular geographical region of interest. As described above, the region of interest is not particularly limited, and may comprise one or more countries. For example, the region of interest can be Europe. Preferably, the region of interest can be Spain, more preferably Iberian Peninsula Spanish territory, in particular Castilla y León, Andalucia and/or Extremadura. Other preferred regions of interest are Italy, The Netherlands, United Kingdom, Australia, Canada and/or United States.

The vaccine of the invention may be administered before the infection, and/or shortly after it. For example, the vaccine of the invention may be administered 1 to 20 days after the outbreak of the disease, preferably 1, or 2, or 3, or 4, or 5, or 6, or 7, or 8, or 9, or 10, or 15, or 20 days after the outbreak of the infection. The vaccine may also be administered 1-4 weeks after the outbreak of the disease, preferably 1, 2, 3 or 4 weeks after the outbreak of the infection.

The vaccine of the invention may be administered by parenteral administration and/or oral administration. Preferably, the vaccine of the invention is administered by parenteral administration, more preferably by subcutaneous and/or intramuscular and/or intradermal administration, and even more preferably by intramuscular administration. For example, the vaccine of the invention may be injected intramuscularly into the neck muscles of swine.

The administered dosage of the vaccine of the invention may range from 1 mL to 5 mL. For example, one dosage of the vaccine of the invention may be 1 mL. For example, one dosage of the vaccine of the invention may be 2 mL.

The administered dosage of the vaccine of the invention, e.g., the single strain vaccine, may comprise between $10^7$ and $10^{12}$ bacteria/dose, preferably between $10^8$ and $10^{10}$ bacteria/dose, more preferably $10^9$ bacteria/dose. The administered dosage of the vaccine of the invention may comprise between $10^8$ and $10^9$ bacteria/mL. The administered dosage of the vaccine of the invention may comprise $10^9$ bacteria/mL. Preferably, the administered dosage of the vaccine of the invention may comprise $5.10^8$ bacteria/mL in a 2 mL/dose.

Accordingly, the preferred total number of bacteria per dose which may be administrated to swine is $10^9$ bacteria.

The vaccine of the present invention, e.g., the single strain vaccine, is an injectable vaccine, preferably an intramuscularly injectable vaccine.

The single strain vaccine of the present invention preferably elicits an immune response based on antibodies. In a further embodiment, the single strain vaccine of the present invention elicits a dose-dependent immune response.

According to the present invention, the vaccine of the present invention may be used to treat or prevent diarrhea. In some embodiments, the vaccine may be used to delay the appearance of clinical signs and/or to reduce the overall severity of diarrhea and/or severe diarrhea. In some embodiments, the vaccine of the present invention may also be used to prevent and/or reduce the time of shedding of *Brachyspira hyodysenteriae*. In some embodiments, the vaccine of the present invention may also be used to help develop diarrhea only at later stages and/or to resolve diarrhea sooner when compared to non-vaccinated animals and/or animals vaccinated with a low-dose vaccine.

Vaccination Protocol

According to the present invention, the vaccine of the invention may be preferably administered to the swine after weaning, most preferably two weeks after weaning. For example, the swine may be vaccinated since the fourth week of life. According to the present invention, the swine may be vaccinated twice (revaccinated). The swine are preferably revaccinated two weeks after the first vaccination. For example, the swine may be vaccinated two weeks after weaning, e.g., at the age of four weeks. Then, the second vaccine (revaccination) may take place at the age of six weeks (i.e., two weeks after the first vaccine was administered). For example, the swine may be vaccinated two weeks after weaning, e.g., at the age of five weeks. Then, the second vaccine (revaccination) may take place at the age of seven weeks. For example, the swine may be vaccinated two weeks after weaning, e.g., at the age of six weeks. Then, the second vaccine (revaccination) may take place at the age of eight weeks. Vaccination for the first time at the age of four weeks is preferred.

Weaning can occur at 21 days of age (La, T. et al., *Veterinary Microbiology* (2004), 102:97-109). Weaning can also occur at 15 days of age, or at any other age, depending on the heard.

Challenge

According to the present invention, the efficiency of the vaccine can be evaluated by challenging animals that were treated with a vaccine of the present invention in comparison to untreated animals or animals that have been treated with a composition with a reduced dose of bacteria compared to the vaccine of the present invention.

According to the present invention, animals can be challenged with a *Brachyspira hyodysenteriae* strain. This strain can be the same or a different strain than the strain CNCM 1-4720. Preferably, the strain is a different strain, and most preferably the strain is the strain B204. B204 is a well-characterized strain and its use as a challenge strain in the regulatory studies was supported by the European Medicines Agency (EMA) after a specific question addressing this issue in an official scientific advice. This strain is deposited in the American Type Culture Collection (ATCC) as ATCC 31212 and publically available. It can be requested for research centers or other accredited facilities. The strain used for the challenge is hereinafter referred to as the "challenge strain".

According to the present invention, the challenge may be performed by inoculating the animals with a composition comprising live bacteria of the challenge strain, preferably strain B-204. Preferably, the inoculum is administered orally. According to the present invention, the inoculum may for example comprise between $10^4$ and $10^{10}$ bacteria of the challenge strain per dose, more preferably between $10^5$ and $10^9$ bacteria of the challenge strain per dose, even more preferably between $10^6$ and $10^7$ bacteria of the challenge strain per dose, and most preferably $5\times10^6$ bacteria of the challenge strain per dose. According to the present invention, the inoculum may for example have a concentration of between $10^4$ and $10^{10}$ bacteria/mL of the challenge strain per dose, more preferably between $10^5$ and $10^9$ bacteria/mL of the challenge strain per dose, even more preferably between $10^6$ and $10^7$ bacteria/mL of the challenge strain per dose, and most preferably $5\times10^6$ bacteria/mL of the challenge strain per dose, each inoculation dose corresponding to 50 mL, wherein three consecutive doses are administered to the animals. The inoculum may be solid or liquid. The inoculum is preferably liquid, and most preferably is a bacterial suspension. The inoculum may for example be administered once, once a week, once every three days, once every two days, once a day, twice a day or several times a day, most preferably once a day. The inoculum may for example be administered over the course of two weeks, over the course of a week, over four days, over three days, over two days or over one day. Most preferably, the inoculum is administered once a day over the course of three days.

To do this, sterile 60 ml syringes may be used. To do this, the plunger may be removed from the syringe and the nozzle may be covered with one finger. Then, the syringe body may be filled with the inoculum. The plunger may then be replaced and the remaining air may be removed. After doing that, the mixture may be introduced directly into the mouth of the animal by expelling the contents of the syringe into the mouth, and checking that the animal takes all the mixture.

According to the present invention, the bacteria to be used for the challenge can for example be obtained by the following steps:

Step 1: Growing the Bacteria on a Plate

The challenge strain, preferably strain B-204, can be seeded in 9 blood agar (BA) plates with a 10 μl sowing loop and can then be incubated at 38.5° C. in anaerobic conditions until hemolysis-growth can be observed (1-2 days). This is called pass 1 (P1). When the strain grows, the absence of contamination can be checked, e.g., under a microscope. If the strain is pure, growth can be collected with a loop, taking agar fragments in depth at the hemolysis edges (which have a better quality of the culture), and can be deposited on a new BA plate. These fragments can be homogenized and spread in zigzag movements along the plate with the loop. Each of the 9 initial plates can then be seeded into 5 BA plates and the resulting 45 plates can be incubated at 38.5° C. in anaerobic conditions until hemolysis-growth (24 hours) can be observed. This is called pass 2 (P2).

Step 2: Obtaining the Inoculum

Once microscopically checked for the absence of contaminants in growth, the plates can be cut into very small fragments, removing the part of agar in which there is no growth (no visible haemolysis). 2.5 liters of BHI can be prepared and autoclaved. In small amounts of this BHI, the agar fragments can be added from the plates and the mixture can be passed through a mortar until no clots remain. Once all the plates are mixed with the BHI and passed through the mortar, bacteria can be counted with a Neubauer chamber.

The time of the challenge is not particularly limited. The animals might be challenged before, during or after the vaccination, or, where the vaccination comprises several administrations, between the administration of said doses. Preferably the challenge is performed after the vaccination, or, where the vaccination comprises several administrations, after the second and/or after the last administration. Most preferably, the challenge is performed three weeks after the second vaccination and/or five weeks after the first vaccination.

Most preferably, the challenge is performed three weeks after the second vaccination and/or five weeks after the first vaccination with 50 ml of a bacterial suspension comprising $10^6$ bacteria/mL of strain B-204, amounting to a total of $5\times10^7$ bacteria, administered orally once a day over the course of three days.

Methods

Measurement of the Rectal Temperature

For determination of the rectal temperature, a digital thermometer may be used. The sensor can be placed in the rectum until the number on the display is constant. Evaluation of fever can be established by means of a numerical score, e.g.: 0 (less than 39.5), 1 (between 39.5 and 40.5) and 2 (higher than 40.5). This classification is a modification from that described by Moore et al. (1996).

Culture and Isolation of *Brachyspira* from Animals

According to the present invention, feces samples can be collected individually from animals. Feces samples can be analyzed by culturing samples in CVS selective media and incubating in anaerobic conditions at 41° C. The signal observed can be the haemolysis produced in the culture media and confirmation of the presence of spirochaetes can be made by phase contrast microscopy. A negative result may be given at seventh day of incubation without haemolysis. All cases in which spirochetes are observed may be verified by duplex PCR.

Duplex PCR to Detect *Brachyspira hyodysenteriae* and *Brachyspira pilosicoli*

In accordance with the present invention, a duplex PCR can be used to confirm the presence of *Brachyspira hyodysenteriae* and *Brachyspira pilosicoli* from isolates from swine feces. For this, detection of a DNA fragment of 526 base pairs (bp) of the tlyA gene of *B. hyodysenteriae* and another fragment of 930 bp of the 16S rRNA gene of *B. pilosicoli* may be performed with PCR with specific primers for these fragments. Further teaching can be found In "Råsbäck T, Fellström C, Gunnarsson A, Aspán A. Comparison of culture and biochemical tests with PCR for detection of *Brachyspira hyodysenteriae* and *Brachyspira pilosicoli*. J Microbiol Methods 66 (2006): 347-353." For example, the sequence from which the fragment of the tlyA gene of *B. hyodysenteriae* is amplified may be the GenBank entry KU215622.1 and the following sequence (SeqID NO: 17):

```
>KU215622.1 Brachyspira hyodysenteriae strain 49
TlyA (tlyA) gene, partial cds
GTAAATATGAGAGATAAAGAAAGAAATTCTCTTTCTATAATAAAATCTTT

CCTTGGATTATAATACTAATATAAATGCGATTAGATGAATATGTGCATAG

TGAAGGCTATACAGAAAGCAGATCTAAAGCACAGGATATAATACTAGCCG

GTTGTGTTTTTGTTAATGGAGTAAAGGTAACTTCTAAGGCTCATAAAATA

AAAGATACTGATAATATAGAAGTTGTTCAGAATATAAAATATGTATCAAG

AGCTGGAGAAAAATTAGAAAAGGCGTTTGTAGAATTTGGAATATCTGTAG

AAAATAAAATATGTTTAGATATAGGAGCTTCTACAGGAGGATTTACAGAT

TGTCTGCTTAAGCATGGTGCTAAAAAAGTTTATGCTCTTGATGTAGGACA

TAATCAGCTAGTTTATAAACTTCGTAATGATAATAGGGTAGTGTCAATAG

AAGATTTCAATGCCAAAGATATAAATAAAGAAATGTTCAATGATGAAATC

CCATCTGTAATAGTAAGTGACGTATCATTTATATCAATAACAAAAATAGC

ACCAATCATATTTAAAGAATTAAATAATTTAGAGTTTTGGGTAACTTTAA

TAAAACCACAATTTGAAGCTGAAAGAGGTGATGTTTCAAAAGGCGGTATA

ATACGAGATGATATACTTAGAGAAAAAATATTAAATAATGCTATTTCAAA

GATAATAGACTGCGGATTTAAAGAAGTTAATAGAACCATCTCTCCTATAA

AAGGTGCTAAAGGTAATATAGAATA
```

The following primers may be used for the amplification:

```
Bh tlyA_F:
                                   (SeqID NO: 18)
5'-GCA GAT CTA AAG CAC AGG AT-3'

Bh tlyA_R:
                                   (SeqID NO: 19)
5'-GCC TTT TGA AAC ATC ACC TC-3'
```

The sequence from which the fragment of the 16S rRNA gene of *B. pilosicoli* is amplified may be the GenBank entry LC259310.1 and the following sequence (SeqID NO: 20):

```
ATGCAGTCGAGCGGGCTTATTCGGGCAACTGGATAAGTTAGCGGCGAACT

GGTGAGTAACACGTAGGTAATCTGCCGTGAAGTGGGGGATAACCCATGGA

AACATGGACTAATACCGCATATACTCTTGCTACATAAGTAGAGTAGAGGA

AAGTTTTTCGCTTCACGATGAGCCTGCGGCCTATTAGCCTGTTGGTAGG

GTAATGGCCTACCAAAGCTACGATAGGTAGCCGACCTGAGAGGGTGACCG

GCCACATTGGGACTGAGATACGGCCCAGACTCCTACGGGAGGCAGCAGCT

GAGAATCTTCCACAATGGACGAAAGTCTGATGGAGCGACATCGCGTGAGG

GATGAAGGCCTTCGGGTTGTAAACCTCGGAAATTATCGAAGAATGAGTGA

CAGTAGATAATGTAAGCCTCGGCTAACTACGTGCCAGCAGCCGCGGTAAT

ACGTAGGAGGCAAACGTTGCTCGGATTTACTGGGCGTAAAGGGTGAGTAG

GCGGATTTATAAGTCTAAGGTGAAAGACCGAAGCTCAACTTCGGGAACGC

CTCGGATACTGTAAGTCTTGGATATTGTAGGGGATGATGGAATTCTCGGT

GTAGCGGTGGAATGCGCAGATATCGAGAGGAACACCTATAGCGAAGGCAG

TCATCTGGGCATTTATCGACGCTGAATCACGAAAGCTAGGGGAGCAAACA

GGCTTAGATACCCTGGTAGTCCTAGCCGTAAACGTTGTACACTAGGTGCT

TCTATTTAAATAGGAGTGCCGTAGCTAACGTCTTAAGTGTACCGCCTGAG

GAGTATGCCCGCAAGGGTGAAACTCAAAGAAATTGACGGGTCCCCGCACA

AGTGGTGGAGCATGTGGTTTAATTCGATGATACGCGAAAAACCTTACCTG

GGTTTGAATTGTTAGATGAATGATTTAGAGATAAGTCAGACCGCAAGGAC

GTTTAACATAGGTGCTGCATGGCTGTCGTCAGCTCGTGTCGTGAGATGTT

GGGTTAAGTCCCGCAACGAGCGCAACCCTCACCCTCTGTTGCTAACGAGT

AATGTCGAGCACTCTTAGGGGACTGCCTACGTTCAAGTAGGAGGAAGGTG

GGGATGATGTCAAGTCCTCATGGCCCTTATGTCCAGGGCTACACACGTGC

TACAATGGCAAGTACAAAGAGAAGCAAGACCGCGAGGTGGAGCAAAACTC

AAAAAAGTTGCCTCAGTTCGGATTGGAGTCTGAAACTCGACTCCATGAAG

TTGGAATCACTAGTAATCGTAGATCAGAACGCTACGGTGAATACGTTCCC

GGGGATTGTACACACCGCCCGTCACGCCATCGGAGTTGGTTTTACC
```

The following primers may be used for the amplification:

```
Bp16S_F:
                                   (SeqID NO: 21)
5'-CAT AAG TAG AGT AGA GGA AAG TTT TT-3'

Bp16S_R:
                                   (SeqID NO: 22)
5'-CTC GAC ATT ACT CGG TAG CAA CAG-3'
```

The template DNA for the PCR may be extracted from a CVS plate or blood agar plate with the isolated strain (visible hemolysis, without defined surface colonies and visible spirochaetes under the microscope). Therefore, a sample may be taken from the hemolytic zone and inserted into a microtube containing 50 μl of dH$_2$O. The sample may then be frozen for 24 hours prior to PCR or boiled for 10-15 minutes. For gram-negative microorganism, these techniques are sufficient to break the cell membrane. After the PCR, the amplified product may be visualized by electrophoresis on an agarose gel and the size of the visible fragments may be used to identify the presence of *Brachyspira hyodysenteriae* and/or *Brachyspira pilosicoli*. Animals that are positive in duplex PCR are declared as excretory animals.

Indirect Enzyme Linked Immunosorbent Essay (ELISA) for the Detection of Antibodies Against *Brachyspira hyodysenteriae*

According to the present invention, an Indirect Enzyme Linked Immunosorbent Essay (ELISA) can be used for the detection and quantification of antibodies against *Brachyspira hyodysenteriae*. This assay can be used in accordance with the present invention in a method of quantifying in sera the IgG produced as an immune response against an infection produced by the bacterial strain *Brachyspira hyodysenteriae* or an immunization against an experimental dysentery vaccine. The indirect ELISA uses an immunoenzymatic technique allowing the detection of IgG antibodies against *Brachyspira hyodysenteriae* in blood sera samples. The test to be used in accordance with the present invention may consist of seven main steps:

1) Coating of the plates: fixation to the solid support (wells) of the whole sonicated bacteria of the vaccine strain H57. Incubation at 4° C. for 18 hours with gentle agitation at 70 rpm.

2) Wash and Blocking step: addition of a carbonate/bicarbonate solution (0.05 M pH 9.6) with bovine serum albumin (1%) that works as a blocking solution of non-specific binding sites. Incubation at 37° C. for 1 hour with gentle agitation at 70 rpm.

3) Prepare microplate map: a control plate sheet filled in with the identification of the sera that are going to be used as samples put in the exact order that are going to be charged in the ELISA plate, negative control (NC) and positive control (PC), all of them in duplicate, is done for every plate processed or every new run of ELISA.

4) Wash and Sera dilution: each serum sample is diluted in a mixture of PBS, Tween and bovine serum albumin to 1/1250 concentration and added to a well sensitized with the antigen. The antibodies (Ab) present in the sample bind with the bacterial Ag coating the bottom of the well. The plate is incubated at 37° C. for 1 hour at 70 rpm.

5) Wash and Addition of conjugate: a monoclonal anti-Immunoglobulin G (IgG) conjugated porcine Immunoglobulin (Ig) is added with a peroxidase enzyme. This anti-IgG is fixed on IgG free epitopes that have not bound to Ag bound to the well and form a complex. Incubate at 37° C. for 1 hour at 70 rpm.

6) Wash and Addition substrate: 100 mg of TMB (3,3',5,5'-Tetramethylbenzidin) are dissolved in 10 ml of DMSO (Dimethylsulfoxid) in a citrate/phosphate buffer is used as substrate, and hydrogen peroxide as the reaction catalyst. When the peroxidase enzyme bound to the conjugate recognizes the substrate, it binds to it and the product is transformed by the oxidation action of the hydrogen peroxide into a blue colored product. Incubation takes place for 10 minutes at room temperature in the dark.

7) Stop and Absorbance reading: the reaction is stopped with sulfuric acid and the colorimetric reading of the corresponding optical densities at 450 nm is recorded:

In presence of IgG in the serum analyzed an intense yellow colored reaction is observed due to the reaction of the enzyme conjugated to the Anti-IgG Ab which has been bound to the added substrate.

In the absence of IgG in the serum analyzed, the anti-IgG Ab has not been bound and has been eliminated in subsequent washes. Therefore there is no colorimetric reaction.

The optical density at 450 nm can therefore be used as a measure for the amount of specific antibodies against *Brachyspira hyodysenteriae*.

Feces Evaluation

Stool quality may be measured in the laboratory based on the aspect of samples collected at specific days, using a three score criteria (0, 2, 4) after the 3rd administration (d0) and at days 8, 13 and 37 (d8, d13, d37). Stool scores are scored 0 for normal or loose consistency, 2 for liquid diarrhea and 4 for mucous or bloody liquid diarrhea, considered severe diarrhea.

Thus, the present invention provides the following items:

1. A composition comprising bacteria from at least two genetically diverse strains of *Brachyspira hyodysenteriae*.

2. The composition according to item 1, wherein the bacteria are inactivated.

3. The composition according to items 1 and/or 2, wherein the bacteria are present in a concentration of at least between $10^8$ and $10^9$ of total bacteria/mL.

4. The composition according to one or more of the preceding items, wherein the genetic diversity is conferred by selecting the at least two genetically diverse strains of *Brachyspira hyodysenteriae* from different clonal complexes.

5. The composition according to one or more of the preceding items, wherein at least one strain belongs to clonal complex II.

6. The composition according to one or more of the preceding items, wherein at least one strain belongs to clonal complex V.

7. The composition according to one or more of the preceding items, wherein at least one strain belongs to clonal complex I.

8. The composition according to one or more of the preceding items, wherein the genetically diverse strains are detected in a proportion of at least 1% in a region of interest with respect to the total of detected strains.

9. The composition according to item 8, wherein the region of interest is Spain.

10. The composition according to one or more of the preceding items, wherein the genetically diverse strains belong to the ancestral type from each clonal complex.

11. The composition according to one or more of the preceding items, wherein the composition further comprises a strain which belongs to a third clonal complex.

12. The composition according to item 11 wherein the third clonal complex is selected from the group comprising clonal complex I, clonal complex II and clonal complex V.

13. The composition according to one or more of the preceding items, wherein at least one of the strains belong to clonal complex I, at least one of the strains belong to clonal complex II and/or at least one of the strains belong to clonal complex V.

14. The composition according to item 13 wherein at least one of the strains is the strain with deposit number CNCM I-4720, at least one of the strains is the strain with deposit number CNCM I-4721 and/or at least one of the strains is the strain with deposit number CNCM I-4722.

15. The composition according to one or more of the preceding items further comprising an adjuvant.

16. The composition according to item 15, wherein the adjuvant is selected from the group consisting of aluminum salts (preferably aluminum hydroxide and/or aluminum phosphate) and mineral oils.

17. The composition according to item 16, wherein the adjuvant is an oil adjuvant, preferably Montanide™ 251 C VG.

18. A composition according to one or more of the preceding items for use as a vaccine.

19. The composition according to item 18, wherein the vaccine is a vaccine against swine dysentery.

20. The composition according to item 19, wherein the swine dysentery is caused by *Brachyspira hyodysenteriae*.

21. The composition according to one or more of items 18 to 20, wherein the vaccine is suitable for administration to swine in a region of interest.

22. The composition according to item 21, wherein the region of interest is Spain.

23. The composition according to one or more of items 18 to 22, wherein the genetically diverse strains are detected in a proportion of at least 1% with respect to the total of detected strains in a region of interest.

24. The composition according to one or more of items 18 to 23, wherein the vaccine is administered by parenteral administration.

25. The composition according to item 24, wherein the vaccine is administered by intra-muscular administration.

26. The composition according to one or more of items 18 to 25, wherein the swine are vaccinated two weeks after weaning.

27. The composition according to item 26, wherein the swine are revaccinated two weeks after the first vaccination.

28. A method for producing a composition according to one or more of items 1 to 27, comprising selecting at least two genetically different strains and mixing them in equal quantity to achieve a concentration of at least between $10^8$ and $10^9$ of total bacteria/mL.

29. The method according to item 28, wherein the at least two genetically different strains are also epidemiologically relevant.

30. The method according to one or more of items 28 to 29, further comprising the inactivation of the bacteria.

31. The method according to one or more of items 28 to 30 wherein the genetic diversity is conferred by selecting each strain from different clonal complexes.

32. The method according to one or more of items 29 to 31, wherein the epidemiologic relevance is conferred by selecting strains that are detected in a proportion of at least 1% with respect to the total of detected strains in a region of interest.

33. The method according to item 32, wherein the region of interest is Spain.

EXAMPLES

Example 1. Multiple-Locus Variable-Number Tandem-Repeat Analysis of *Brachyspira hyodysenteriae*

MVLA Analysis

A set of 172 porcine *B. hyodysenteriae* isolates and strains was used in this study, including the three reference strains B204$^R$ (ATCC 31212), B234$^R$ (ATCC 31287) and WA1$^R$ (ATCC 49526) and the type strain B78$^T$ (ATCC 27164).

Duplicates of the B204$^R$ and B78$^T$ strains were obtained from the bacterial collections held at the University of Leon and Murdoch University. The strains and field isolates were from Spain (n=115), Australia (n=36), Canada (n=3), the United States (n=7), the United Kingdom (n=4), and Netherlands (n=7) and had been recovered from the 1970s to 2009. Twenty-three isolates were recovered from Iberian pigs, a local Spanish breed. These pigs contribute to the preservation of the "dehesa," a specific Mediterranean ecosystem located in the western regions of the country (Castilla y León, Extremadura, and Andalucia), where they are traditionally reared in extensive units. The field isolates were recovered from different herds, except for 26 Spanish isolates that were additionally isolated from 11 herds on different sampling occasions. *B. hyodysenteriae* isolates from the University of León and Murdoch University bacterial collections were identified and cultured, and DNA was extracted in each supplying laboratory by previously reported methods. Working dilutions of extracted DNA were prepared by adjusting them to 1 to 20 ng/μL using a NanoDrop 1000 UV-Vis spectrophotometer (Thermo Scientific, Wilmington, Del.).

Identification of Tandem Repeats and Primer Design

The chromosomal DNA sequence of *B. hyodysenteriae* WA1$^R$ was retrieved from GenBank (accession no. NC_012225) and investigated for potential tandem repeats using the default parameters of the Tandem Repeat Finder program, available as a Web service (hypertext transfer protocol://tandem.bu.edu/). The selected tandem-repeat loci were ranked by consensus length, and those with lengths between 25 and 300 bp were used to design primers within the flanking regions. Loci were named Bhyo, followed by the repeat length ranking number (from 1 to 23), separated by an underscore.

Tandem-Repeat Screening and MLVA Setup

In a preliminary step, DNA extracted from *B. hyodysenteriae* strain B204$^R$ was used to estimate the empirical annealing temperature of the 23 selected primer pairs in a gradient PCR. The PCR was run in a Mastercycler Gradient (Eppendorf Scientific Inc., Westbury, N.Y.) with an initial step of 95° C. for 5 min, followed by 30 cycles of a three-step cycle protocol consisting of 94° C. for 30 s, 56±8° C. for 30 s, and 72° C. for 1 min and a final extension step of 72° C. for 10 min. To screen the usefulness of the 23 selected loci as epidemiological markers, DNA samples of *B. hyodysenteriae* strains B204$^R$ and B78$^T$ and isolates 3, 19, 23, 53, 64, H9, and H72, which have been shown to have genetic differences by PFGE and RAPD in a previous investigation (Hidalgo, Á. et al., Epidemiology & Infection (2010), 138:76-85), were used. In addition, tandem-repeat data generated for *B. hyodysenteriae* strain WA1$^R$ were taken into account. Each locus was amplified individually, and the length of the product was analyzed by conventional agarose gel electrophoresis using a 100-bp DNA ladder (Invitrogen, Carlsbad, Calif.). Loci were selected according to their length polymorphism and their ability to generate amplicons for most of the DNA samples tested. To confirm the length of the PCR product, as well as the number of repeats, the consensus patterns, and the sizes of the flanking regions, amplicons were purified using the AxyPrep PCR Cleanup kit (Axygen Biosciences, Union City, Calif.) and sequenced by using fluorescently labeled dideoxynucleotide technology according to the manufacturer's recommendations (Applied Biosystems, Foster City, Calif.). On this basis, eight VNTR loci were selected to be used in the final typing tool.

PCR Amplifications for MLVA

The isolates obtained with the bacterial collection selected for this study were analyzed by independently amplifying the eight selected VNTR loci in a Mastercycler apparatus (Eppendorf). The primers for PCR and thermocycling conditions used are described in Table 1. PCR mixtures were prepared using 0.2-mL sterile tubes containing 1×PCR buffer (20 mM Tris HCl [pH 8.4], 50 mM KCl), 5 mM MgCl$_2$, 1 U of Platinum Taq DNA polymerase (Invitrogen), 200 μM deoxynucleoside triphosphate mix (Invitrogen), 0.2 μM each forward and reverse primers, 2 μL of the DNA working dilution, and sterile distilled water up to a final volume of 50 μL. PCR products were resolved in agarose gels, and their allelic sizes were estimated using a 100-bp DNA ladder (Invitrogen). Amplicons of alleles not detected in the setup step were sequenced as described above. In addition, in order to ensure the repeatability of the technique, 28 DNA samples were randomly selected and tested again. Reproducibility between laboratories was assessed by independent determination of the VNTR types of 14 isolates at the University of León and Murdoch University.

A 25 µl volume was used for multiplex PCR amplification with a thermal cycling protocol of 95° C. for 15 min; 30 three-step cycles of 94° C. for 30 s, 55/53° C. (set 1/set 2) for 90 s, and 72° C. for 90 s; and a final extension step of 72°

TABLE 1

Primers for PCR and thermocycling conditions.

| Primer | Sequence | Thermocycling program |
|---|---|---|
| Bhyo_6 | SEQ ID NO. 1: F, AAATATAACTCATATTCATAACAAG SEQ ID NO. 2: R, AGAGAACTTCAAAAAACTTC | 30 x (94° C. for 20 s, 52° C. for 20 s, 72° C. for 30 s), 72° C. for 5 min |
| Bhyo_7 | SEQ ID NO. 3: F, AGTAATAAATTAAAAAATCTCTAGGGTGG SEQ ID NO. 4: R, GGTTTGGTAGAACAATCTGC | 30 x (94° C. for 20 s, 59.5° C. for 20 s, 72° C. for 30 s), 72° C. for 5 min |
| Bhyo_12 | SEQ ID NO. 5: F, CGTATGATTATTTTACTTGTCAG SEQ ID NO. 6: R, TTTTATTACAGCAACTTTACTC | 30 x (94° C. for 30 s, 59° C. for 30 s, 74° C. for 40 s) |
| Bhyo_17 | SEQ ID NO. 7: F, TTTTTGCCATAAATATCTCTC SEQ ID NO. 8: R, GAAATGCCGTCCTTCTTAG | 30 x (94° C. for 30 s, 59° C. for 30 s, 74° C. for 40 s) |
| Bhyo_21 | SEQ ID NO. 9: F, AAAATAATGATGAAGTATCTAATG SEQ ID NO. 10: R, AAGTATCAGGTAAAGGTAAATC | 30 x (94° C. for 20 s, 52° C. for 20 s, 72° C. for 30 s), 72° C. for 5 min |
| Bhyo_22 | SEQ ID NO. 11: F, AGATTAAAAACTGACGGAG SEQ ID NO. 12: R, AGCACAAGAACCTTCAAAC | 30 x (94° C. for 30 s, 55° C. for 30 s, 72° C. for 60 s), 72° C. for 5 min |
| Bhyo_10 | SEQ ID NO. 13: F, CTCTCTTTTATATTTTTATTATAGTTG SEQ ID NO. 14: R, TTGATGAAATTAGACCATTC | 30 x (94° C. for 30 s, 55° C. for 30 s, 72° C. for 40 s), 72° C. for 5 min |
| Bhyo_23 | SEQ ID NO. 15: F, CACCCTTTAGACTTATTATTTTATTTTG SEQ ID NO. 16: R, TTGTTCTGCGTGCGTGTAG | 30 x (94° C. for 30 s, 55° C. for 30 s, 72° C. for 40 s), 72° C. for 5 min |

The eight primer pairs used in the individual PCRs were grouped into two sets (set 1 and set 2); labeled fluorescently with 6-carboxyfluorescein (6-FAM™), VIC®, PET®, or NED™ (Applied Biosystems) at the 5'-end of the forward primers; and pooled prior to performing a multiplex PCR using the Qiagen Multiplex PCR kit according to the manufacturer's recommendations (Qiagen, Germantown, Md.).

TABLES 2 and 3

| Primer sets | | |
|---|---|---|
| Primer | Fluorescence | Final concentration |
| Primer set 1 | | |
| Bhyo_7 | 6-FAM ™ | 0.25 µM |
| Bhyo_12 | VIC ® | 0.25 µM |
| Bhyo_17 | NED ™ | 0.15 µM |
| Bhyo_22 | PET ® | 0.15 µM |
| Primer set 2 | | |
| Bhyo_6 | 6-FAM ™ | 0.25 µM |
| Bhyo_10 | PET ® | 0.25 µM |
| Bhyo_21 | VIC ® | 0.15 µM |
| Bhyo_23 | NED ™ | 0.15 µM |

C. for 10 min Multiplex PCR products were diluted 1:10 in distilled water before 1 µl of this dilution was mixed with 0.5 µl of 1200 LIZ Size Standard (Applied Biosystems) and 10.5 µl of formamide After the mixture was heated for 3 min at 96° C. and rapidly cooled on ice, GeneScan analysis was performed using an ABI 3730 DNA analyzer (Applied Biosystems). The freely available program Peak Scanner Software v 1.0 (Applied Biosystems) was used to size the PCR fragments for each locus.

Data Analysis

The number of repeats was calculated according to the following formula:

Number of repeats=[Fragment size (bp)×Flanking regions (bp)]/Repeat size (bp).

The results were approximated to the nearest lower integer and sequentially scored (Bhyo_6, Bhyo_7, Bhyo_12, Bhyo_17, Bhyo_21, Bhyo_22, Bhyo_10, and Bhyo_23) to create a numerical profile that defined each strain. When PCR amplification was undetectable, the assigned number of repeats was 99. MLVA profiles were ascribed to MLVA types by assigning a whole number. Isolates were considered genetically identical when the numerical profiles for all eight loci matched. The Hunter-Gaston diversity index was used to measure the polymorphism of individual loci and the index of discrimination of the MLVA typing method for the eight combined VNTR loci (Hunter, P. R. and M. A. Gaston, Journal of Clinical Microbiology (1988), 26:2465-2466). Approximate 95% confidence intervals (CI) were calculated as described by Grundmann et al. (Journal of Clinical Microbiology (2001), 39:4190-4192). Redundant isolates (n=26) were removed prior to calculating the previous indexes. The Sequence Type Analysis and Recombinational Tests (START2) program, available for free at hypertext transfer protocol://pubmlst.org/software/analysis/start2/, was used to analyze the MLVA profiles and types of the spirochetes tested. A phylogenetic tree of the MLVA types was constructed based on the unweighted-pair group method using average linkages (UPGMA) clustering strategy. A bootstrap analysis for 1,000 replicates was undertaken using FreeTree at hypertext transfer protocol://web.natur.cuni.cz/flegr/programs/freetree.htm. The goeBURST algorithm, available at hypertext transfer protocol://goeburst.phyloviz.net/#Software, a global implementation of the eBURST algorithm (Feil, E. J. et al., Journal of Bacteriology (2004), 186:1518-1530.), was used to identify groups of related genotypes of B. hyodysenteriae at single-, double-, and triple-locus variant levels. Population structure was tested as proposed by Smith et al. (Proceedings of the National Academy of Sciences U.S.A. (1993), 90:4384-4388), taking into account the modifications proposed by Haubold et al. (Genetics (1998), 150:1341-1348.) for the calculation of the critical value (LMC) of the distribution of the variance of the pairwise differences (VD), and expressed as a standardized index of association (ISA).

Results

Identification of VNTR Markers

Investigation of the chromosomal sequence of B. hyodysenteriae WA1$^R$ with the Tandem Repeat Finder program identified 404 repeats in tandem through the whole chromosome, with 135 repeats/Mbp. Subsequent selection of the most suitable tandem-repeat markers decreased the number to be included in the MLVA to 23, which were consecutively named Bhyo_1 to Bhyo_23 and used to design primers within the flanking regions. Fifteen loci that were monomorphic or failed to amplify all or most of the nine selected isolates with the specific primers were discarded. The remaining eight loci were polymorphic, with different allele sizes. Sequencing of the PCR products confirmed that the length polymorphism was due to differences in the copy number of tandem repeats and that the consensus pattern, its period size, and the flanking regions were stable (Table 4). Therefore, eight loci (Bhyo_6, Bhyo_7, Bhyo_12, Bhyo_17, Bhyo_21, Bhyo_22, Bhyo_10, and Bhyo_23) were included in the MLVA scheme for B. hyodysenteriae. These loci were distributed from position 1236667 to position 2949421 of the WA1R genome (Table 4). Four loci, Bhyo_6, Bhyo_10, Bhyo_21, and Bhyo_22, were placed in open reading frames encoding hypothetical proteins, while the other four were located in intergenic regions. Bhyo_7 was placed between the genes for methyl-accepting chemotaxis protein McpA and a hypothetical protein. Bhyo_12 was between the genes for a putative glycosyltransferase family 2 protein and a hypothetical protein. Bhyo_17 was between the genes for glycerol 3-phosphate dehydrogenase and ferredoxin. Bhyo_23 was between the genes for a hypothetical protein and putative RarR, predicted to be a permease

TABLE 4

Features of the loci included in the MLVA

| Locus | Size (bp) of repeat | Flanking region | Position |
| --- | --- | --- | --- |
| Bhyo_6 | 156 | 78 | 1236667-1237672 |
| Bhyo_7 | 135 | 177 | 1818959-1819765 |
| Bhyo_10 | 111 | 88 | 1754196-1755095 |
| Bhyo_12 | 105 | 59 | 2949083-2949421 |
| Bhyo_17 | 76 | 175 | 1690628-1691034 |
| Bhyo_21 | 33 | 195 | 1396843-1397034 |
| Bhyo_22 | 30 | 153 | 2597474-2597543 |
| Bhyo_23 | 26 | 102 | 1838685-1838736 |

MLVA Typing

The set of eight VNTR markers was used to type the full collection of 174 B. hyodysenteriae strains and isolates recovered from pigs in several countries (including the duplicates of B78$^T$ and B204$^R$). The strains and isolates were efficiently amplified, and the lengths of the PCR products were converted into numbers of repeats. Sequencing of new alleles that were identified at this stage confirmed that the length differences represented variations in the number of the previously detected repeat motifs. The marker Bhyo_10 was the most diverse VNTR, with eight different numbers of repeats (99, 2, 3, 5, 6, 7, 8, and 10), with an assigned number of repeats of 99 because of a lack of amplification. Seven numbers of repeats were detected for locus Bhyo_17, while markers Bhyo_6, Bhyo_7, and Bhyo_21 each presented six numbers of repeats. Loci Bhyo_12 and Bhyo_22 showed a discontinuous distribution of four numbers of repeats. VNTR marker Bhyo_23 showed less diversity, with only two different numbers of repeats, 1 and 2, detected. An accurate estimation of the degree of polymorphism of the loci was achieved by means of the Hunter-Gaston diversity index, with the discrimination powers of the loci ranging from 0.141 to 0.764. Locus Bhyo_10 was the most discriminatory, with a value of 0.764, followed by loci Bhyo_7, Bhyo_6, Bhyo_17, and Bhyo_21, with values of 0.761, 0.718, 0.71, and 0.699, respectively. Loci Bhyo_12 and Bhyo_23 had diversity indexes of 0.472 and 0.318, respectively, while the most conserved locus was Bhyo_22, with a polymorphism index of 0.141.

The Hunter-Gaston discriminatory index of the MLVA typing method at eight loci for 146 strains and isolates from different herds was 0.938 (95% CI, 0.9175 to 0.9584). Analysis of the combination of the eight VNTR loci for all of the B. hyodysenteriae isolates and strains showed 44 MLVA types, which differed by at least one repeat for one of the eight loci among two different types. The MLVA types of the reference strains were type 35 for WA1$^R$, type 23 for B204$^R$, and type 10 for B234$^R$, while the type strain B78$^T$ was assigned to MLVA type 28. Analysis of the different MLVA types in each country showed the existence of considerable diversity. There were 15 types (1, 2, 3, 5, 9, 11, 12, 13, 14, 18, 19, 20, 22, 24, and 37) found among the 89 Spanish isolates from different herds, 16 types (15, 16, 17, 25, 26, 31, 32, 33, 34, 35, 36, 38, 39, 42, 43, and 44) among the 36 Australian isolates, 2 types (21 and 27) for the three Canadian isolates, 3 types (3, 6 and 41) for the seven from Netherlands, 4 types (3, 8, 29, and 30) for the four strains from the United Kingdom, and 6 types (4, 7, 10, 23, 28, and 40) for the seven isolates and strains from the United States.

MLVA type 3 was shared by isolates from Spain, the United Kingdom, and Netherlands. The MLVA types were stable for the herds where more than one isolate was recovered on different sampling occasions. B. hyodysenteriae strain WA1$^R$ showed a mismatch for locus Bhyo_6 between the length of the PCR product, 780 bp (four numbers of repeats), and the data derived from the sequenced genome, 1,092 bp (six numbers of repeats). Isolates and strains included in the repeatability and reproducibility tests had the same MLVA types at the different testing times. Moreover, each of the duplicates of the *B. hyodysenteriae* type and reference strains, B78$^T$ and B204$^R$, from the University of Leon and Murdoch University collections, generated the same MLVA patterns.

MLVA Types and Bacterial Population Analysis

An evolutionary tree based on MLVA profiles and constructed according to the UPGMA clustering strategy for the 44 MLVA types of *B. hyodysenteriae* determined in this study is shown in FIG. 1. MLVA type relationships at the single-, double-, and triplelocus variant levels depicted with the goeBURST algorithm are shown in FIG. 2. Six clonal complexes (I to VI) were established at the single-locus variant level. Three new groups appeared when investigating double-locus variants, while three single locus variant groups (II, III, and IV) were clustered together at this level. When high-level edges were displayed to study relationships at the triple-locus variant level, a large cluster appeared which included groups I to IV, and group V was expanded by two more types. MLVA types 4, 5, 10, and 15 were not linked with any of the other types detected at any of the levels studied. Population linkage disequilibrium was detected for the 146 isolates from different herds ($I^{SA}$=0.1359; P<0.001) and for the different MLVA types ($I^{SA}$=0.0336; P=0.005).

Example 2. Selection and Culture of the Universal Vaccine Strains

Figure 3:
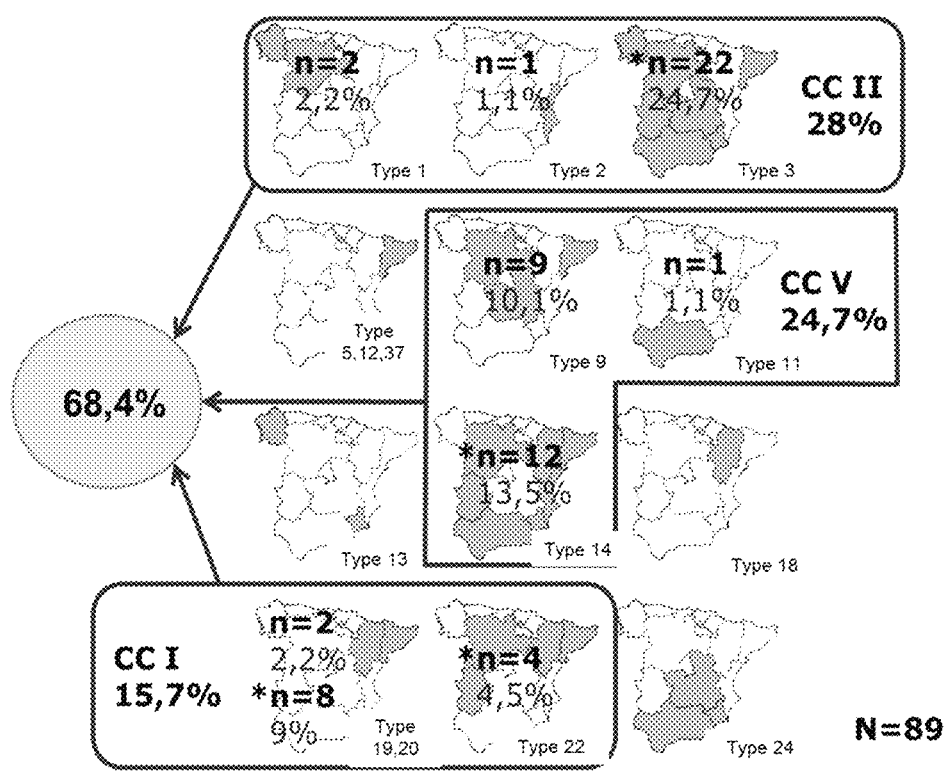
FIG. 3. Selection of the strains of the universal vaccine of the examples ("Type 3" (e.g. strain with deposit number CNCM I-4720), "Type 14" (e.g. the strain with deposit number CNCM I-4721) and "Type 20" (e.g. the strain with deposit number CNCM I-4722). The ancestral type strain of the referred clonal complexes (II, V and I) was selected. The selected strains are detected in a proportion of at least 1% with respect to the total of detected strains in Spain.

Three *Brachyspira hyodysenteriae* strains were selected, each of which belongs to different clonal complexes (clonal complexes I, II and V). Each genetically diverse selected strain belongs to the ancestral type from each clonal complex. Moreover, each selected strain is at least 1% detected with respect to the total of detected strains in Spain (FIG. 3). The strains are the ones deposited within the *Collection Nationale de Cultures de Microorganismes* (CNCM), Institut Pasteur, on Mar. 14, 2013, with registration numbers CNCM I-4720, CNCM I-4721 and CNCM I-4722.

The strain with registration number CNCM I-4720 belongs to clonal complex II. The strain with registration number CNCM I-4721 belongs to clonal complex V. The strain with registration number CNCM I-4722 belongs to clonal complex I.

CNCM I-4720 is 24,7% detected with respect to the total of detected strains in Iberian Peninsula Spanish territory. CNCM I-4721 is 13,5% detected with respect to the total of detected strains in Iberian Peninsula Spanish territory. CNCM I-4722 is 9% detected with respect to the total of detected strains in Iberian Peninsula Spanish territory.

The isolated bacteria (free from contaminants) are inoculated in agar-blood plates. The plates are kept in anaerobic conditions at 39.5° C. for 4-5 days, until hemolysis in the whole plate is observed. Agar fragments at the hemolysis borders and they are inoculated in a new agar-blood plate, incubated in the same conditions. Bacteria are passed to a new agar-blood plate and, in parallel, to a Fastidious Anaerobe Agar (FAA) plate, and bacteria are cultured in the same conditions during 3-4 days. The bacteria can then be transferred to liquid growth medium, and cultured.

For fermentation, bacteria are incubated in approx. 4 L of suitable culture medium (such as Brain Heart Infusion media from Merck) at 38,5° C. with light agitation (50 rpm) in an oxygen-free atmosphere. The fermentation occurs until the optical density is approx. 1.6 (or until there are around 10$^9$ UFC/mL (usually between 15 and 30 hours)).

Example 3. Inactivation of the Bacteria

After fermentation, 4 L (approx.) of culture are pumped into a sterile flask and centrifuged (2×7000 rpm, 10 minutes). Resulting pellets are suspended in 1 L sodium acetate buffer 0.1 M. The inactivation of the culture is carried out with an injection of formaldehyde at 0.5% and incubation during 24 hours at 37° C. with light agitation (50 rpm). Next day the suspension is centrifuged and resuspended in sterile sodium acetate 0.1 M. The antigen (10$^9$-10$^{10}$ bacteria/mL, approx.) is kept at 4° C. until mixing with adjuvant and excipients for vaccine manufacturing.

Example 4. Vaccine Formula (Universal Vaccine of the Invention)

The vaccine comprises the following components. The term antigen refers to the above-mentioned selected *Brachyspira hyodysenteriae* strains, and the final concentration of antigen is 10$^9$ bacteria/mL in an equal mixture of the three selected strains.

| Component | Quantity (for 2 L of vaccine) | Percentage/final concentration in the vaccine |
|---|---|---|
| Antigen | 200 mL | 10$^9$ bacteria/mL |
| Montanide IMS 251 C VG (Seppic) | 400 mL | 20% |
| Thimerosal 5% (Sigma) | 4 mL | 0.01% |
| Sodium acetate 0.1M (Boente) | 1400 mL | |

The components were mixed by agitation at 4° C. overnight.

Example 5. Comparison Between an Efficient Autovaccine and the Universal Vaccine of the Invention The following conditions were used:
1.—The pigs used in this example came from a farm free of spirochaetal infections and with low health status, due to the difficulty to achieve a good challenge in pigs with high health status.
2.—The diet was manipulated in order to induce a very high dysbiosis in the intestine. The importance of diet in swine dysentery is also well known. In this experiment the feed was mixed with a 50% of soy flour that had 46% of protein. Pigs received this diet from the day of the challenge on (10 days in total).
3.—The strain used for the challenge was the reference strain B204 (ATCC Number: 31212). The strain was previously passed three times in pigs to fully maintain its pathogenicity and to verify that the experimental infection would be appropriate. This ensures that the strain used has a high pathogenicity and causes a severe disease in infected pigs.

The following three groups of six pigs each were used:
  Group 1 (autovaccine): piglets were vaccinated via intramuscular (i.m.) with the autovaccine (inactivated B204 and adjuvant, same protocol as above but with inactivated B204 as antigen) at 6 weeks of life and revaccinated at 8 weeks of life. Each dose contained $10^9$ bacteria.

Group 2 (universal vaccine): piglets were vaccinated via i.m. with the universal vaccine (the polyvalent inactivated and adjuvanted vaccine, comprising the three selected field strains). The vaccination protocol was the same as above (piglets were vaccinated at 6 weeks of life and revaccinated at 8 weeks). The dose was also $10^9$ bacteria in an equal mixture of the three selected strains.

Group 3 (control group, unvaccinated): the same adjuvant (without bacterial antigen) was injected i.m. to piglets at 6 and 8 weeks of life (same protocol as above).

Vaccination and revaccination were performed in the farm. The piglets were kept on the farm until the $10^{th}$ week of age and were then moved to the experimental facilities of the University of León. Piglets belonging to the three experimental groups were mixed among them in these facilities.

The experimental infection was made 3 weeks after the second dose, when piglets were 11 weeks old. Every pig of each group received 100 mL of a fresh culture of B204 type strain containing $10^9$ bacteria/mL orally during 3 consecutive days. The diet was modified at first day of challenge, as mentioned above.

Since the first day of challenge (PID 1) pigs were daily sampled by collecting rectal swabs and faecal shedding of *B. hyodysenteriae* was monitored by microbiological culture. From PID 1 on, general health status and presence or diarrhoea and characteristics of the faeces were also recorded.

Results:
1.—Mortality

| | MORTALITY | | |
|---|---|---|---|
| | Dead pigs (total) | % | PID (post-infection days) |
| Group 1 (Universal vaccine) | 1 (6) | 14.2 | 29 |
| Group 2 (Autovaccine) | 1 (6) | 14.2 | 29 |
| Group 3 (Control) | 3 (6) | 50 | 7, 9, 13 |

In the group of pigs vaccinated with the universal vaccine, one piglet died in the $17^{th}$ day after experimental infection. In this case, death was caused by pneumonia. The death pig had not eliminated *Brachyspira hyodysenteriae* in faeces before its death.

Mortality caused by swine dysentery was the same in the group of pigs vaccinated with the universal vaccine and those vaccinated with the autovaccine (1 pig in each group) and three times lower than in the unvaccinated pigs of the control group (3 pigs died).

Given the Odds ratio, mortality risk was 6 times higher in those animals from the control group as compared with those vaccinated with the universal vaccine or with the autovaccine (OR=6; CI 95% 0.28-246.02).

Figure 4:
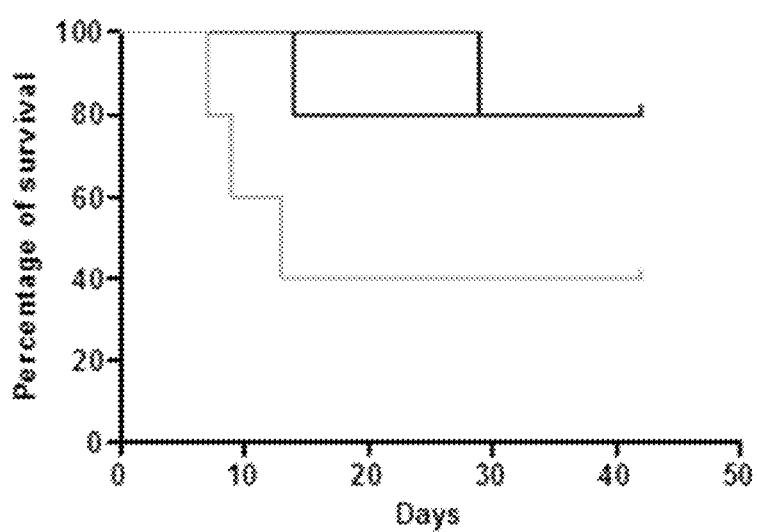
FIG. 4. Survival curves comparing the groups vaccinated with the autovaccine (dark grey), universal vaccine (black) and non-vaccinated (control, light grey), using the Log Rank test at α=0.05.
Figure 5:
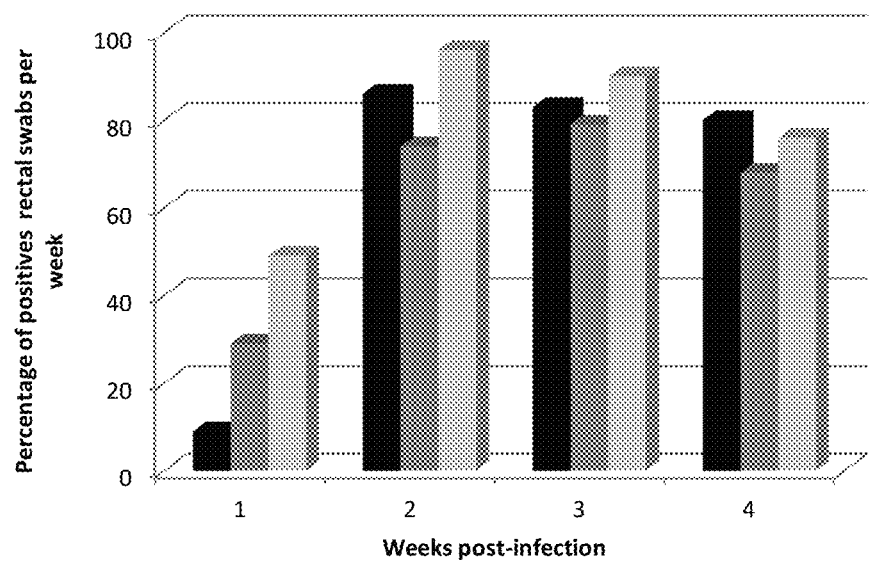
FIG. 5. Elimination of *B. hyodysenteriae* over the time post-challenge (percentage of positives rectal swabs per week) (black, autovaccine; dark grey, universal vaccine; light grey, non-vaccinated animals (control)).

In both groups of vaccinated pigs (those vaccinated with the universal vaccine and those vaccinated with the autovaccine) the death of the pig occurred at day 29 post-challenge, whereas in the control group the three pigs died on days 7, 9 and 13 post-challenge (FIG. 4).

As expected, no difference was observed between survival curves of vaccinated with the universal vaccine and autovaccinated animals (p=0.9372).

2.—Incubation Period

| | INCUBATION PERIOD | | | | |
|---|---|---|---|---|---|
| | Mean (days) | Standard deviation | Minimum (days) | Maximum (days) | Mode (days) |
| Group 1 (Universal vaccine) | 5.8 | 2.28 | 3 | 8 | 8 |
| Group 2 (Autovaccine) | 7.6 | 2.07 | 4 | 9 | 8 |
| Group 3 (Control) | 4 | 2.283 | 1 | 6 | 6 |

Figure 6:
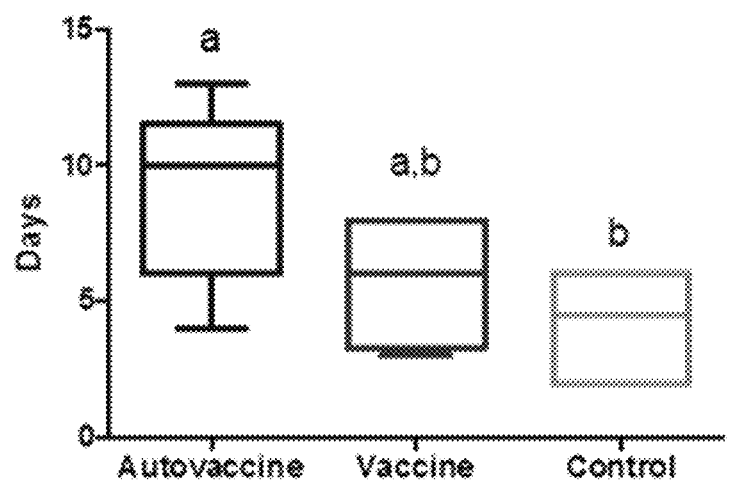
FIG. 6. Incubation period (number of days between the challenge and the appearance of diarrhoea or faecal shedding of the bacteria) in the different groups (black, autovaccine; dark grey, universal vaccine; light grey, non-vaccinated animals (control)).

The incubation period, defined as the number of days between the challenge and the appearance of diarrhoea or faecal shedding of the bacteria was significantly longer in those pigs from the control group as compared with autovaccinated animals (F=7.36; p=0.024). This incubation period was also higher for vaccinated pigs as compared with controls. No statistically significant differences were found between both groups of vaccinated and autovaccinated pigs (F=1.7; p=0.228) (FIG. 6).

3.—Diarrhoea and Bloody Diarrhoea

| | DIARRHOEA | | |
|---|---|---|---|
| | Days sampled | Days with diarrhoea Total days (%) | Days with bloody diarrhoea Total days (%) |
| Group 1 (Universal vaccine) | 167 | 58 (34.73) | 20 (11.97) |
| Group 2 (Autovaccine) | 160 | 63 (39.35) | 11 (6.85) |
| Group 3 (Control) | 122 | 64 (52.46) | 35 (28.69) |

The proportion of days with diarrhoea was significantly higher in the control group as compared with vaccinated pigs with the universal vaccine ($Chi^2$=8.37; p=0.004) and with autovaccinated pigs ($Chi^2$=4.27; p=0.038).

A similar result regarding the proportion of days with bloody diarrhea was obtained. The value was significantly higher in the control group as compared with vaccinated group with the universal vaccine ($Chi^2$=7.25; p=0.007) and autovaccinated group ($Chi^2$=16.6; p<0.001).

Figure 7:
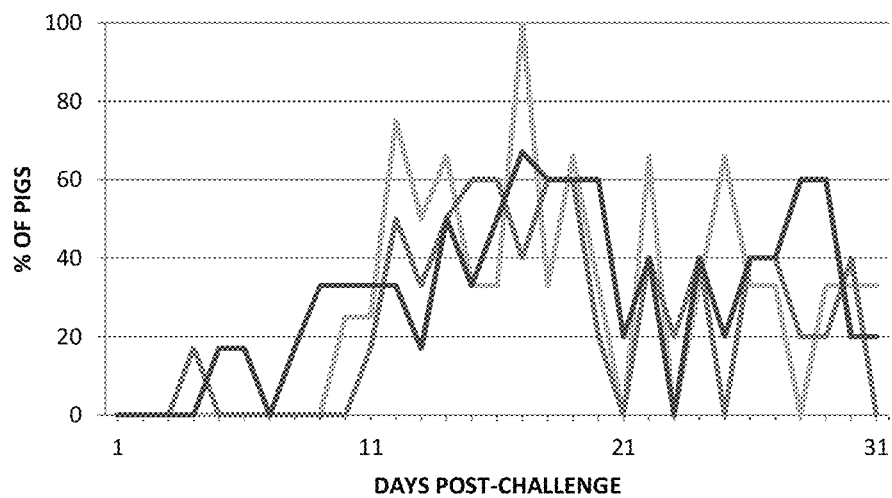
FIG. 7. Percentage of pigs with diarrhoea (a) and bloody diarrhoea (b) after challenge (black, autovaccine; dark grey, universal vaccine; light grey, non-vaccinated animals (control)).
Figure 7:
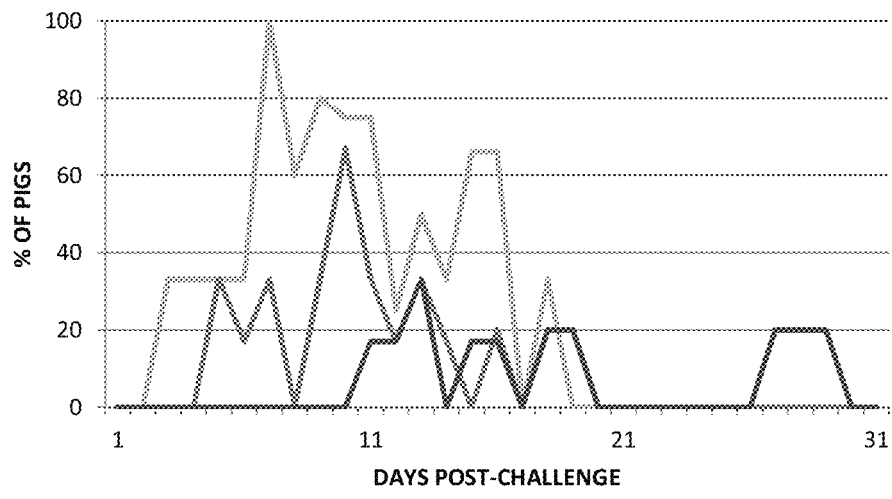

In addition, the bloody diarrhoea began earlier in the control group (two days post challenge). In this group all pigs had bloody diarrhoea on day 6 post-challenge and for 5 days the bloody diarrhoea affected more than 50% of pigs (FIG. 7).

No statistically significant differences were found between vaccinated with the universal vaccine and autovaccinated pigs in the proportion of days with diarrhoea ($Chi^2$=0.57; p=0.45) nor with bloody diarrhoea ($Chi^2$=1.92; p=0.165).

4.—Average Daily Gain

| | Average daily gain at 9 days post-challenge | |
|---|---|---|
| | ADG (kg) | Standard deviation |
| Group 1 (Universal vaccine) | 0.05 | 0.249 |
| Group 2 (Autovaccine) | 0.27 | 0.372 |
| Group 3 (Control) | −0.29 | 0.308 |

In the first 9 days after challenge, almost no weight gain was observed in pigs from the vaccinated with the universal vaccine group and a mean daily gain of 0.27 kg was determined in animals from the autovaccinated group. However, no significant differences were demonstrated when comparing both groups. These groups showed no weight loss at any time during the whole trial.

| | Average daily gain at 24 days post-challenge | |
|---|---|---|
| | ADG (kg) | Standard deviation |
| Group 1 (Universal vaccine) | 0.24 | 0.263 |
| Group 2 (Autovaccine) | 0.13 | 0.212 |
| Group 3 (Control) | 0.20 | 0.185 |

Figure 8:
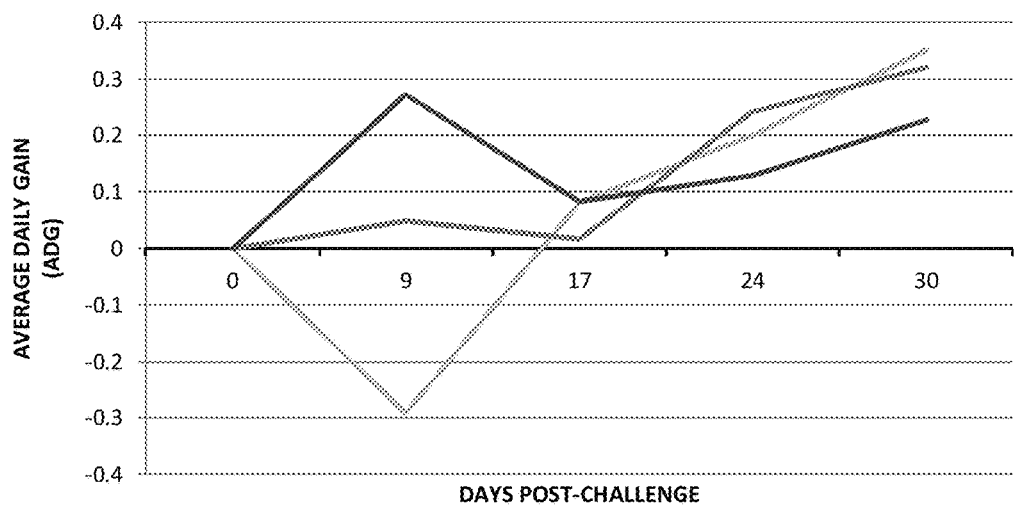
FIG. 8. Average daily gain (ADG) on the post-challenge days (black, autovaccine; dark grey, universal vaccine; light grey, non-vaccinated animals (control)).
Figure 9:
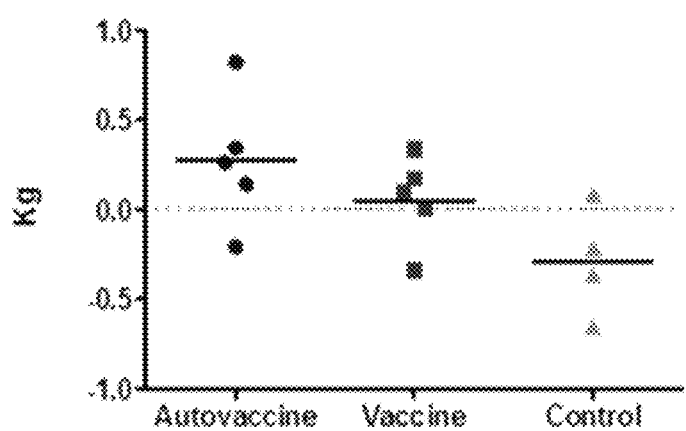
FIG. 9. Daily weight gain (DWG) in the first 9 days after challenge (day 0 to day 9) (black, autovaccine; dark grey, universal vaccine; light grey, non-vaccinated animals (control)).

Animals from the control group showed a clear loss of weight during the first 9 days after challenge. The average weight loss was 0.29 kg/day. After these 9 days, significant differences were not found in the average daily gain (ADG) of survivor pigs of the control group compared with that of pigs of vaccinated with the universal vaccine and autovaccinated groups (FIGS. 8 and 9).

Animals from the autovaccinated group showed the lower average daily gain when analyzing at 24 days post challenge, probably as a consequence of the longer incubation period of the disease in these animals. On the other hand, animals from the vaccinated with the universal vaccine and control groups showed a clear recovery of daily weight gain at this moment since they were affected previously by clinical disease.

Conclusions

The objective of the study was to compare the effectiveness of a universal vaccine (in this case composed by three selected strains, none of which was the strain causing the infection) with that of an autovaccine in very stringent conditions.

- The infection of pigs with B204 strain using three daily doses of $10^9$ bacteria and inducing a high dysbiosis in the intestine causes severe swine dysentery and a mortality of 50% of untreated pigs in the control group.
- There are no differences in the effectiveness of the universal vaccine and the autovaccine in the reduction of mortality caused by swine dysentery.
- There are not statistically significant differences in the effectiveness of the universal vaccine and the autovaccine in the reduction of clinical signs of swine dysentery (diarrhoea and bloody diarrhoea).
- There was no weight loss in pigs vaccinated with the universal vaccine neither in those vaccinated with the autovaccine.

The effectiveness of the universal vaccine is comparable with the effectiveness of an effective autovaccine. The universal vaccine has a good cost/benefit relationship for the control of swine dysentery in field conditions, considering the tested effectiveness of the autovaccines.

Example 6. Lipopolysaccharide (LPS) ELISA Study of Hiperimmunized Rabbits

The aim of the following study was to show the qualitative differences found between the serological immune response of each of the three strains (A, B and C, see below for the exact reference) contained in the trivalent Brachyspira hyodysenteriae vaccine formula (universal vaccine).

Material and Methods

For the experiment, nine rabbits were separated in three groups of three animals and each group was intravenous inoculated with one of the strains during six days (D1, D2, D3, D4, D5 and D10 of the study) with 0.5 mL of the bacterial suspension. Thus, for each bacteria was necessary the preparation of 0.5 ml×3 animals per strain×6 days=9 ml of $10^{10}$ bacteria/mL culture.

The inoculum was prepared from a pure liquid culture of each strain in 100 ml BHI (Brain Heart Infusion) with 6% BFS (Bovine Fetal Serum). Liquid culture was centrifuged and washed three times with PBS Buffer; initial suspension (growth to $10^9$ bacteria/mL aprox.) was concentrated ten times to a final suspension $10^{10}$ bacteria/mL.

Blood was collected days D15, D18, D21, D24, D27 and D36 from each animal. Sera were sent immediately to Aquilon facilities for antibody analysis.

ELISA plates were coated separately with 0.5 µg LPS antigen of each strain, obtained as described in Hassan et al. (Antibody response to experimental Salmonella typhimurium infection in chickens measured by ELISA (1990). Vet rec. 126(21):519-22) and ELISA was performed following the method for Salmonella described by Collazos (Aportaciones al diagnostico y control de la salmonelosis porcina (2008). Tesis Doctoral. Universidad de León).

| ELISA designation | Laboratory ID | Deposit code |
|---|---|---|
| A | H57 | CNCM I - 4720 |
| B | H170 | CNCM I - 4721 |
| C | H219 | CNCM I - 4722 |

Results

Figure 10:
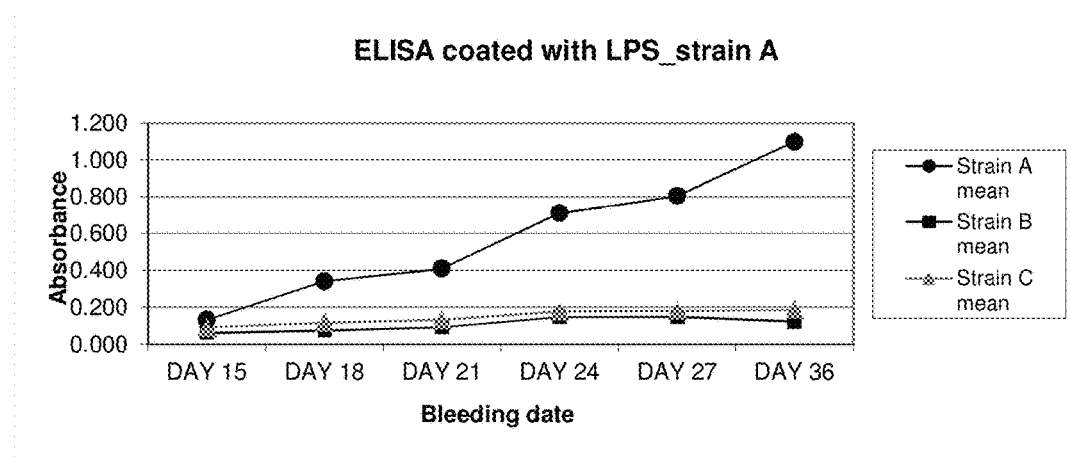
FIG. 10. Measurement of the antibody response (the absorbance at 450 nm directly correlates to amount of antibody produced) of the hiperimmunized rabbits with A, B and C strains against LPS of strain A (CNM 1-4720) along the experiment (potency assay).
Figure 11:
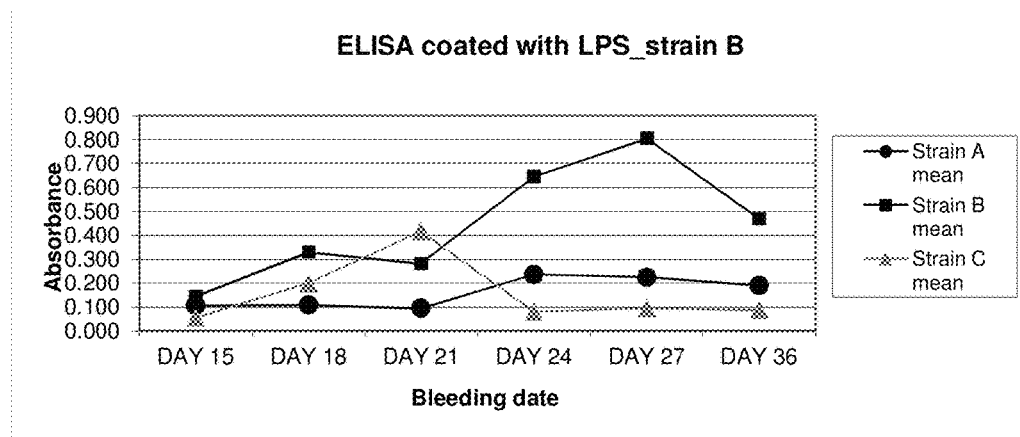
FIG. 11. Measurement of the antibody response (the absorbance at 450 nm directly correlates to amount of antibody produced) of the hiperimmunized rabbits with A, B and C strains against LPS of strain B (CNM 1-4721) along the experiment (potency assay).
Figure 12:
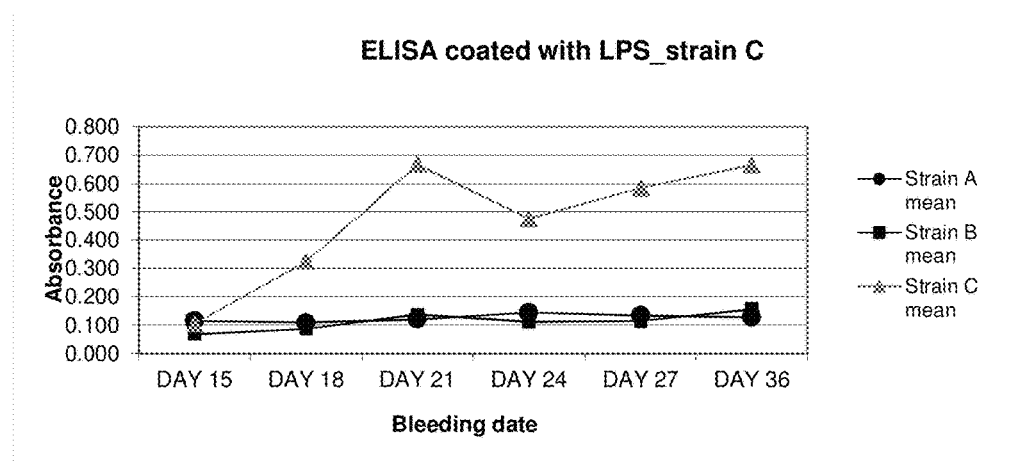
FIG. 12. Measurement of the antibody response (the absorbance directly correlates to amount of antibody produced) of the hiperimmunized rabbits with A, B and C strains against LPS of strain C (CNM 1-4722) along the experiment (potency assay).
Figure 13:
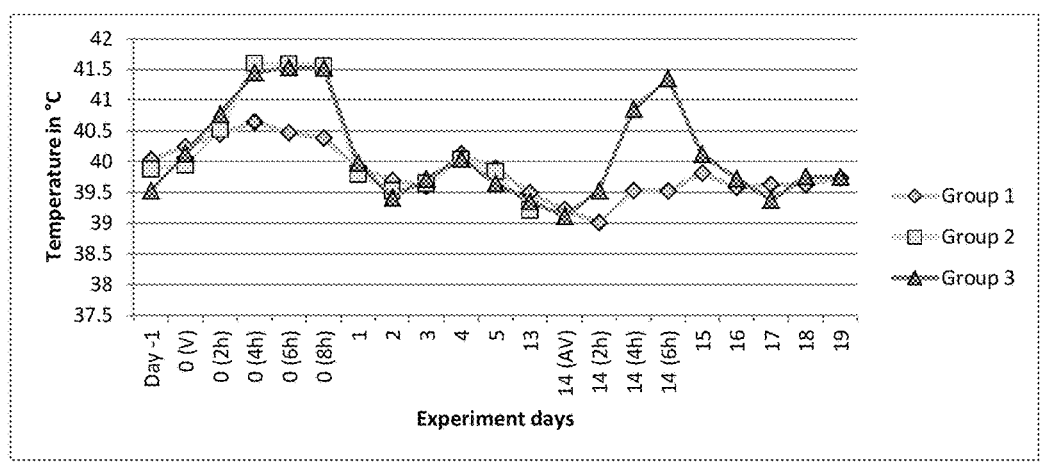
FIG. 13. Rectal temperature of the animals in the pre-regulatory safety study. Grey: animals treated with a physiological solution (group 1), light grey: animals that received the vaccine of the present invention once at day 0 (group 2), dark grey: animals that received the vaccine of the present invention twice, once at day 0 and once at day 14 (group 3). Each group consisted of 8 animals.
Figure 14:
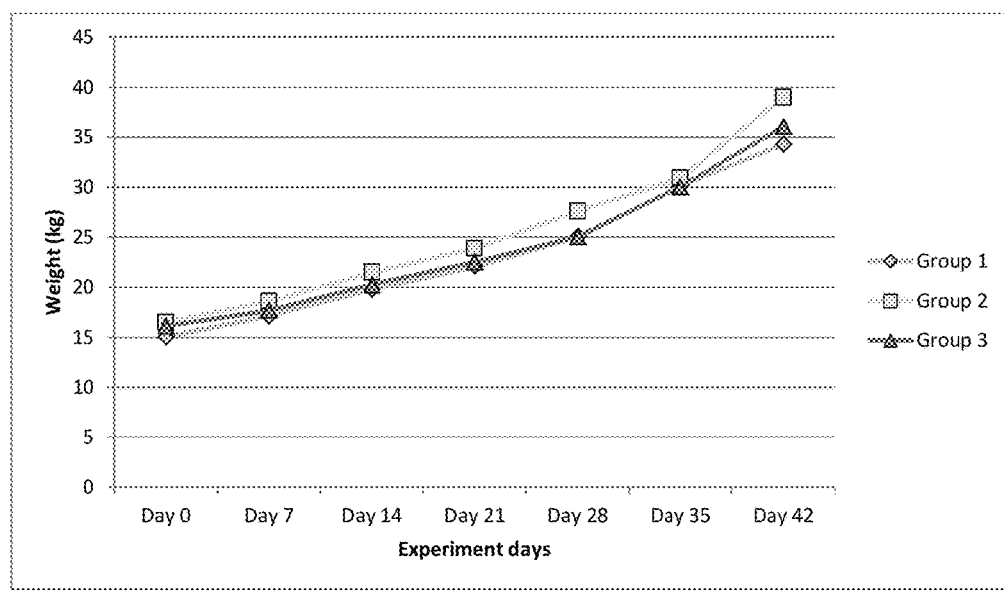
FIG. 14. Mean weight of the animals in the pre-regulatory safety study. Grey: animals treated with a physiological solution (group 1), light grey: animals that received the vaccine of the present invention once at day 0 (group 2), dark grey: animals that received the vaccine of the present invention twice, once at day 0 and once at day 14 (group 3). Each group consisted of 8 animals.
Figure 15:
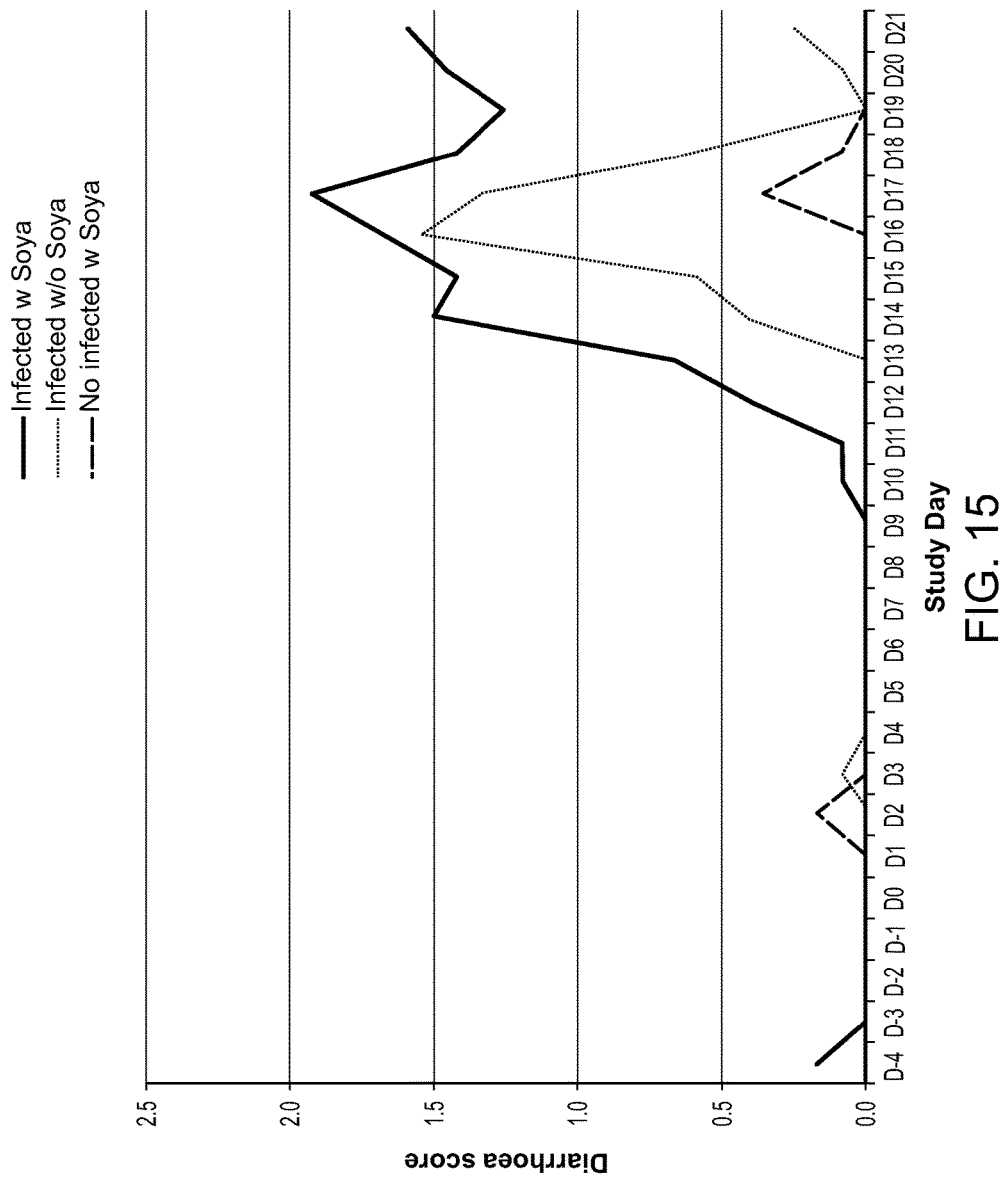
FIG. 15. Diarrhea evaluation after challenge of untreated animals. Dark grey: animals challenged with the challenge strain and fed with hyperproteic (soy rich) feed. Light grey: animals challenged with the challenge strain and fed with normal feed. Medium grey: unchallenged animals fed with hyperproteic (soy rich) feed.
Figure 16:
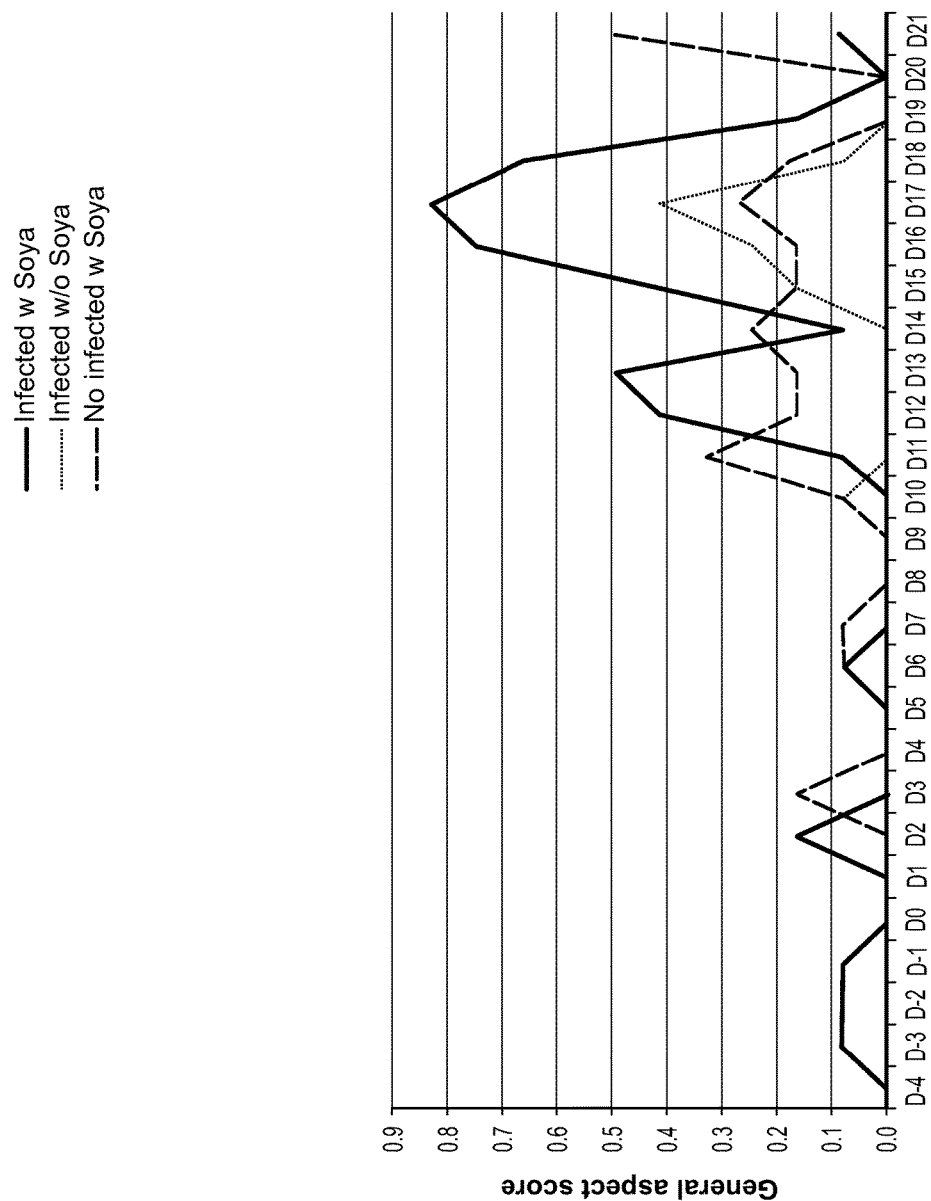
FIG. 16. General aspect evaluation after challenge of untreated animals. The following parameters were evaluated: dyspnoea, nasal discharge, cough, conjunctivitis, sneezing, paralysis, discoordination, lethargy, vomiting, external aspect. 0: not altered, 1: mild/moderate alteration, 2: severe alteration. Dark grey: animals challenged with the challenge strain and fed with hyperproteic (soy rich) feed. Light grey: animals challenged with the challenge strain and fed with normal feed. Medium grey: unchallenged animals fed with hyperproteic (soy rich) feed.

The results can be seen on FIGS. 10, 11 and 12. Differences between ELISA plates coated with LPS coming from the three spirochaete strains against sera of a group of rabbits hiperimmunized with these three strains separately can be observed. It has been demonstrated that the sera immune response produced by each of the spirochaete strain here used (A, B and C) is different depending on whether the LPS coating of the ELISA plate is homologous or heterologous to the sera strain (see FIGS. 10, 11 and 12). These results confirm the fact that genetically separated strains show a specific antibody production. Accordingly, the inventors have been able to surprisingly detect differences in the immune response/animal's antibody production due to immunization with the bacteria that were selected on the basis of their genetic diversity, as described in the application, and this genetic diversity criteria is not functional sequence-driven. These unexpected results justify the inclusion of several antigenic patterns in the vaccine formula, especially taking into account that the genetic criteria used is not "gene-driven", but just based in genomic polymorphism.

Example 7. Culture of the Universal Vaccine Strain

A Brachyspira hyodysenteriae strain deposited within the Collection Nationale de Cultures de Microorganismes (CNCM), Institut Pasteur, on Mar. 14, 2013, with registration numbers CNCM I-4720 (hereinafter referred to as strain of the present invention) was selected. The strain belongs to the ancestral type of clonal complex II of *Brachyspira hyodysenteriae*.

The isolated bacteria (free from contaminants) were inoculated in agar-blood plates. The plates were kept in anaerobic conditions at 39.5° C. for 4-5 days until hemolysis areas spread by the agar plates were observed. Agar fragments at the hemolysis borders were inoculated in a new agar-blood plate, and incubated in the same conditions. The bacteria were passed to a new agar-blood plate and, in parallel, to a Fastidious Anaerobe Agar (FAA) plate, and bacteria were cultured in the same conditions for 3-4 days. The bacteria were then transferred to liquid growth medium and cultured.

For fermentation, bacteria were incubated in approx. 4 L of suitable culture medium (such as Brain Heart Infusion media from Merck) at 38.5° C. with light agitation (50 rpm) in an oxygen-free atmosphere. The fermentation occured until the optical density is approx. 1.6 (or until there were around $10^9$ UFC/mL (usually between 15 and 30 hours)). From all testedstrains, only the strain CNCM I-4720 was able to grow at an industrial scale.

Example 8. Inactivation of the Bacteria

After fermentation, 4 L (approx.) of culture were pumped into a sterile flask and centrifuged (2×7000 rpm, 10 minutes). Resulting pellets were suspended in 1 L sodium acetate buffer 0.1 M. The inactivation of the culture was carried out with an injection of formaldehyde at 0.5% and incubation during 24 hours at 37° C. with light agitation (50 rpm). On the next day the suspension was centrifuged and resuspended in sterile sodium acetate 0.1 M. The antigen ($10^9$-$10^{10}$ bacteria/mL, approx.) was kept at 4° C. until mixing with adjuvant and excipients for vaccine manufacturing.

Example 9. Vaccine Formula (Universal Vaccine of the Invention)

The vaccine used for the following examples comprises the following components. The term antigen refers to the above-mentioned selected *Brachyspira hyodysenteriae* strain, and the final concentration of antigen is $10^9$ bacteria/2 mL dose for the normal vaccine and $10^7$ bacteria/2 mL dose for the subpotent/reduced dose vaccine.

TABLE 5

Composition of the vaccine.

| Component | Quantity (for 2 L dose of vaccine) | Percentage/final concentration in the vaccine |
|---|---|---|
| (A) Composition of the normal vaccine dose (2 L) | | |
| Antigen | 200 ml in Sodium Acetate 0.1M | $10^9$ bacteria/ 2 mL dose |
| Montanide IMS 251 C VG (Seppic) | 400 mL | 20% |
| Sodium acetate 0.1M (Boente) | 1400 mL | |
| (B) Composition of the reduced vaccine dose for dose confirmation study (2 L) | | |
| Antigen | 200 ml in Sodium Acetate 0.1M | $10^7$ bacteria/ 2 mL dose |

TABLE 5-continued

Composition of the vaccine.

| Component | Quantity (for 2 L dose of vaccine) | Percentage/final concentration in the vaccine |
|---|---|---|
| Montanide IMS 251 C VG (Seppic) | 400 mL | 20% |
| Sodium acetate 0.1M (Boente) | 1400 mL | |

The components were mixed by agitation at 4° C. overnight. For the following experiments, a single dose of the vaccine of the present invention refers to a dose as disclosed in Table 5, comprising 2 ml solution with a total of $10^9$ bacteria per dose in the case of the normal dose and $10^7$ bacteria per dose in the case of the reduced dose (the subpotent vaccine).

Example 10. Pre-Regulatory Safety Study

The study was performed to test of the innocuousness of the Swine dysentery vaccine formulation. Three groups of 8 animals were tested in controlled facilities for the evaluation of regulatory safety parameters (see Table 6). The vaccine as described in Example 9 or, in case of group 1, a physiological infusion was administered to the animals.

TABLE 6

Animal groups used for the pre-regulatory safety study

| GROUP | ADMINISTRATION | DOSIS | TRIAL DAY | ANIMALS |
|---|---|---|---|---|
| 1 | Physiological infusion | 2 ml | D 0, D 14 | 8 |
| 2 | Vaccine | 2 ml | D 0 | 8 |
| 3 | Vaccine | 2 ml | D 0, D 14 | 8 |

The animals were studied with regard to abnormal behavior and systemic reactions such as dyspnoea, mucus, cough, diarrhoea, vomit, paralysis, motile dysfunctions, somnolence, depression and external appearance for at least 14 days after each inoculation. No signs of abnormal behavior and systemic reactions were observed in any animal at any moment of the experiment.

The animals were studied daily with regard to local reactions at the injection site until day 14. No local reactions at the injection site were observed in any animal at any moment of the experiment.

The rectal temperature was measured at day −1 of first vaccine inoculation, in the administration moment and after 2, 4, 6 and 8 hours post-injection. After that, the temperature was recorded daily 5 days after vaccine injection. The same measurement pattern was carried out for the second inoculations. The results are shown in FIG. 17 and indicate that the injection of the test vaccine in pigs in this trial caused a significant but transitory increase of the temperature of the animals that reverted after 24 hours post inoculation. This fact was observed in both inoculations at day 0 and day 14 of the experiment.

The weights of study animals were recorded through a calibrated scale at days 0, 7, 14, 21, 28, 35 and 42. The results are shown in FIG. 18. It can be concluded that the weight development was similar in the different groups.

Example 11. Inoculation Model with *Brachyspira hyodysenteriae* B 204 from Culture Plates The following Standard Operating Procedure was developed in order to obtain an inoculum from blood agar plates of *Brachyspira hyodysenteriae* strain B204, ATCC 31212 for later use in the development of an infection (i.e. challenge of the animals).

Step 1: Growing the Bacteria on a Plate

The strain, which was stored at −80° C., was seeded in 9 blood agar (BA) plates with a 10 μl sowing loop and incubated at 38.5° C. in Anaerobic conditions until hemolysis-growth was observed (1-2 days). This was called pass 1 (P1).

When the strain grew, the absence of contamination was we checked under a microscope. If the strain was pure, growth was collected with a loop, taking agar fragments in depth at the hemolysis edges (which had a better quality of the culture), and deposited on a new BA plate.

These fragments were homogenized and spread in zigzag movements along the plate with the loop. Each of the 9 initial plates was seeded into 5 BA plates and the resulting 45 plates were incubated at 38.5° C. in anaerobic conditions until hemolysis-growth (24 hours) was observed. This was called pass 2 (P2).

Step 2: Obtaining the Inoculum

Once microscopically checked for the absence of contaminants in growth, the plates were cut into very small fragments, removing the part of agar in which there was no growth (no visible haemolysis). Previously, 2.5 liters of BHI was prepared and autoclaved. In small amounts of this BHI, the agar fragments were added from the plates and the mixture was passed through a mortar until no clots remain. Once all the plates were mixed with the BHI and passed through the mortar, bacteria were counted with a Neubauer chamber, and required to reach a concentration of $10^6$ bacteria/ml.

Step 3: Inoculation of Animals

Each animal to be infected received orally 50 ml of the mixture. To do this, sterile 60 ml syringes were used. The plunger was removed from the syringe and the nozzle was covered with one finger. Then, the syringe body was filled with 50 ml of the mixture. The plunger was then replaced and the remaining air was removed. After doing that, the mixture was introduced directly into the mouth of the animal by expelling the contents of the syringe into the mouth, and checking that the animal takes all the mixture.

Example 12. Effect of Different Feeds on the Challenge

The objective of the study was to establish an infection model for swine dysentery, disclosing the role of the pre-challenge high protein level in the diet on the clinical outcome. For this purpose, animals were infected with 50 ml of a bacterial culture of *B. hyodysenteriae*, strain B204, with approximately $5 \times 10^6$-$10^7$ bacteria/ml, as described in Example 11.

TABLE 7

Groups used in the challenge test

| Group | Management |
| --- | --- |
| Group 1 | 12 pigs orally infected with *B. hyodysenteriae* and fed with hyperproteic feed during 5 days pre-challenge |
| Group 2 | 12 pigs orally infected with *B. hyodysenteriae* with standard feed |
| Group 3 | 12 pigs not infected and fed with hyperproteic feed during 5 days pre-challenge |

As can be seen from FIGS. 15-18, the challenge was sufficient to infect the challenged groups with diarrhea. In particular the challenge of the pigs fed with hyperproteic feed resulted in animals with a high amount of diarrhea occurrence and reduced body weight compared to the non-infected group.

Figure 17:
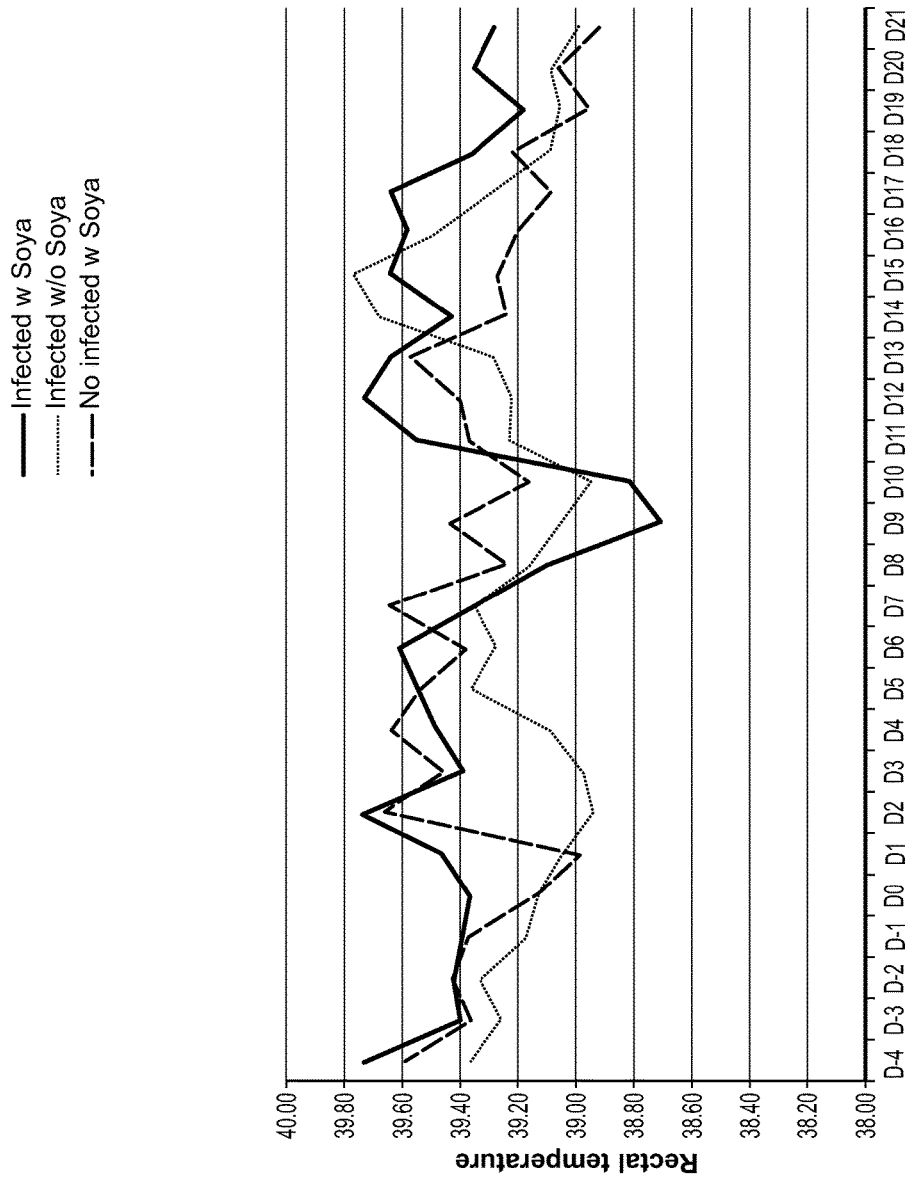
FIG. 17. Rectal temperature of untreated animals after challenge. Dark grey: animals challenged with the challenge strain and fed with hyperproteic (soy rich) feed. Light grey: animals challenged with the challenge strain and fed with normal feed. Medium grey: unchallenged animals fed with hyperproteic (soy rich) feed.

For determination of the rectal temperature, a digital thermometer was used. The sensor was placed in the rectum until the number on the display was constant. Evaluation of fever was established by means of a numerical score: 0 (less than 39.5), 1 (between 39.5 and 40.5) and 2 (higher than 40.5). This classification is a modification from that described by Moore et al. (1996). Animals scored 2 were considered to have fever. The rectal temperature of the untreated animals is shown in FIG. 17.

Figure 18:
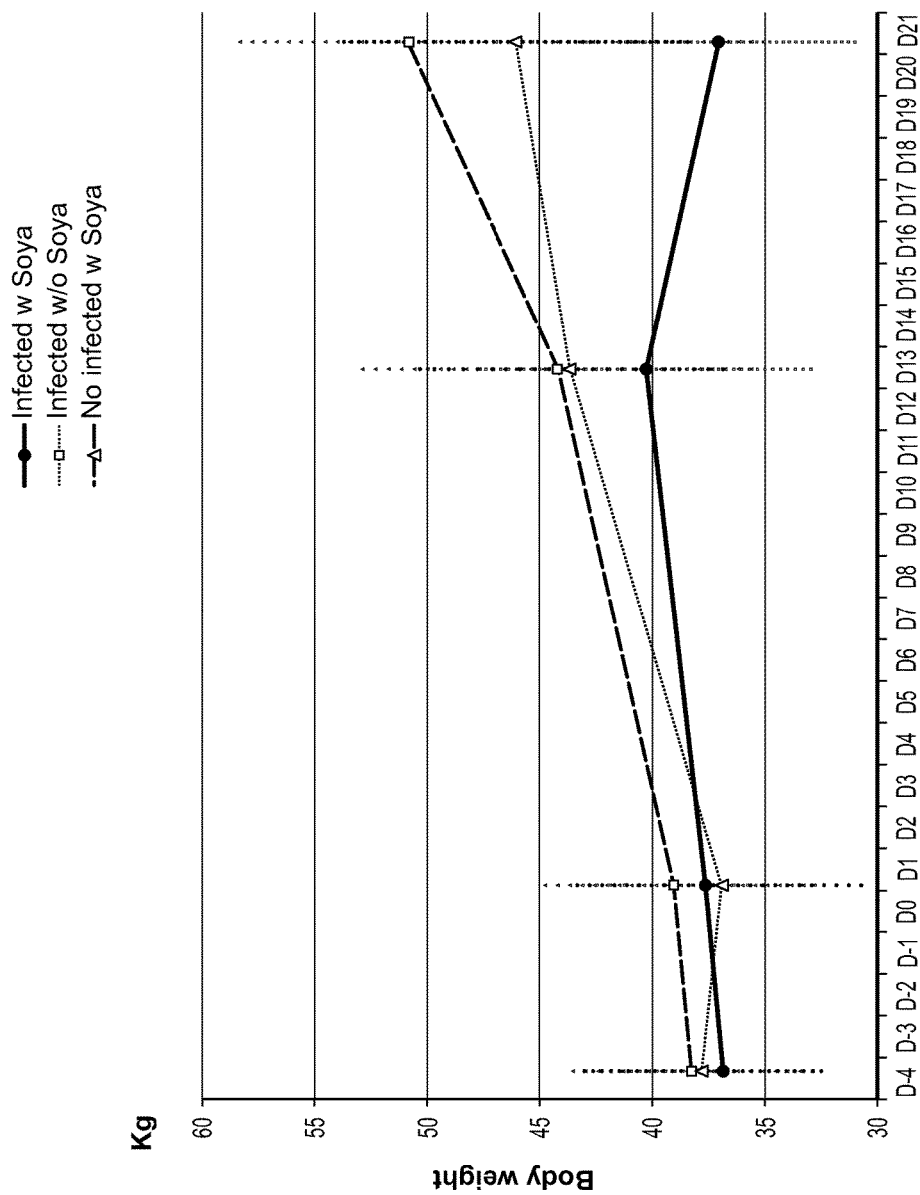
FIG. 18. Average body weight of untreated animals after challenge. Dark grey: animals challenged with the challenge strain and fed with hyperproteic (soy rich) feed. Light grey: animals challenged with the challenge strain and fed with normal feed. Medium grey: unchallenged animals fed with hyperproteic (soy rich) feed.

Animals were weighed at arrival (to perform the randomization while maintaining a weight balance between the three groups), at challenge (D0), and on days D4, D15 and D22. The average body weights are shown in FIG. 18.

As a result, it can be concluded that the experimental infection of 10 weeks old pigs by oral route with 50 ml of *B. hyodysenteriae* suspension adjusted to $10^6$-$10^7$ bacteria/ml per day resulted in a solid model that can be used in the vaccine's efficacy studies. The model was more complete when animals were fed with a hyperproteic diet during five days before the experimental infection.

The clinical signs (diarrhoea, fever, negative effect on body weight), the intestinal lesions, and the shedding of *B. hyodysenteriae* in faeces observed in the animals infected with *B. hyodysenteriae* five days after the ingestion of hyperproteic diet were observed in almost all the animals included in the experimental groups.

Example 13. Design of the Vaccination and Challenge Experiments

Figure 19:
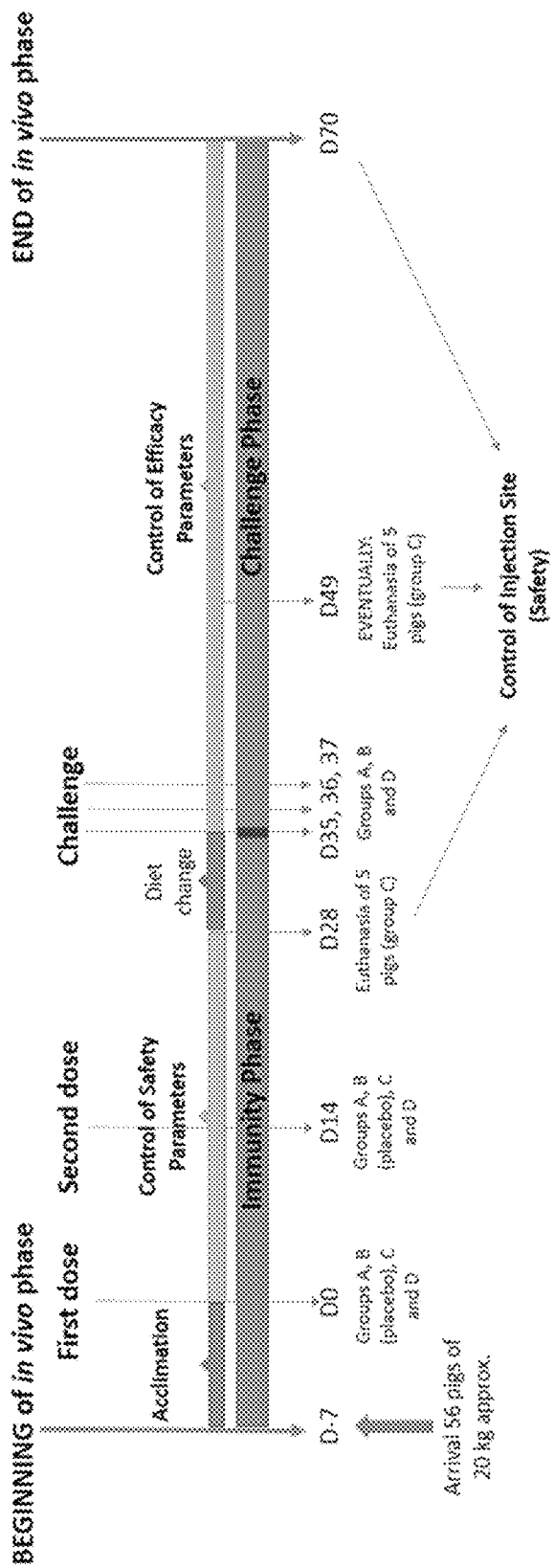
FIG. 19. Schedule for the vaccination experiment with challenge. All animals were sacrificed at day 71 of the trial.

Fifty-six cross-breed healthy pigs were randomly grouped into four pens in order to test the efficacy, safety, safety of the injection site and to justify the dose of the vaccine of the present invention swine dysentery vaccine against *B. hyodysenteriae*. The groups were blind managed by the personnel involved in the clinical monitoring. FIG. 19 shows an overview of the challenge protocol used. In general, the challenge protocol with the hyperproteic feed developed in Example 12 was used. In general, animals were treated with the vaccines described in Example 9 or the placebo on days 0 and 14 and their diet was changed to a high protein diet according to Example 12 on day 28. The animals were first vaccinated at an age of 6 weeks. This age ensures that there is no influence of maternal immunity, which can be an issue when testing the vaccine at an earlier age.

TABLE 8

Pig groups used in the experiments

| Group | n | Day 0 | Day 14 | Challenge | Objective |
| --- | --- | --- | --- | --- | --- |
| Vaccine | 15 | $1^{st}$ vaccination | $2^{nd}$ vaccination | D 35, 36, 37 | Normal vaccine dose ($10^9$ bacteria/dose) for dose confirmation, safety and efficacy studies |
| Placebo | 15 | Placebo | Placebo | D 35, 36, 37 | Control for dose confirmation, safety and efficacy studies |

TABLE 8-continued

Pig groups used in the experiments

| Group | n | Day 0 | Day 14 | Challenge | Objective |
|---|---|---|---|---|---|
| Sub-potent | 15 | 1$^{st}$ vaccination | 2$^{nd}$ vaccination | D 35, 36, 37 | Reduced vaccine dose (10$^7$ bacteria/dose) for dose confirmation study |

Vaccinated groups were compared with the non-vaccinated or control group in terms of safety (general clinical signs, rectal temperature, body weight control, evaluation of the injection site) and, after challenge with the reference strain B204, in terms of efficacy (onset of immunity) by the evaluation of different parameters. Selected efficacy parameters are aimed to evaluate the disease signs and the production losses in the porcine production (general clinical signs, rectal temperature, diarrhoea evaluation, spirochetes excretion and serology (ELISA test)).

Example 14. Challenge of Vaccinated, Vaccinated with a Eeduced Dose and Non-Vaccinated Animals The animals from Example 13 that were inoculated received daily doses of 50 mL of a *B. hyodysenteriae* culture of strain B204 at a concentration of 1×10$^6$ live bacteria/mL during study days 35, 36 and 37 which amounts to about 5×10$^7$ bacteria/day according to the inoculation protocol described in Example 11. For the administration of the bacterial suspension the animals were first visually identified and then they were fed manually and individually with a 60 mL syringe the stated volume of inoculum. After voluntary ingestion of the required amount of inoculum each animal was marked on the back with a wax crayon. Animals were feed deprived 12 hours before challenge and water deprived 6 hours before challenge during the three challenge days (D35, D36 and D37).

Example 15. Results of the Challenge Study

Indirect Enzyme Linked Immunosorbent Essay (ELISA) for the Detection of Antibodies Against *Brachyspira hyodysenteriae*

An Indirect Enzyme Linked Immunosorbent Essay (ELISA) was used for the detection and quantification of antibodies against *Brachyspira hyodysenteriae*. This assay is used to quantify in sera the IgG produced as an immune response against an infection produced by the bacterial strain *Brachyspira hyodysenteriae* or an immunization against an experimental dysentery vaccine. The indirect ELISA uses an immunoenzymatic technique allowing the detection of IgG antibodies against *Brachyspira hyodysenteriae* in blood sera samples. The test consisted of seven main steps:

1) Coating of the plates: fixation to the solid support (wells) of the complete antigen (Ag) of the vaccine strain H57. Incubation at 4° C. for 18 hours with gentle agitation at 70 rpm.
2) Wash and Blocking step: addition of a blocking solution of non-specific binding sites. Incubation at 37° C. for 1 hour with gentle agitation at 70 rpm.
3) Prepare microplate map: a control plate sheet with the samples identification, negative control (NC) and positive control (PC), all of them in duplicate, was done for every plate processed or every new run of ELISA.
4) Wash and sera dilution: each serum sample was diluted to 1/1250 concentration and added to a well sensitized with the antigen. The antibodies (Ab) present in the sample bind with the bacterial Ag coating the bottom of the well. The plate is incubated at 37° C. for 1 hour at 70 rpm.
5) Wash and addition of conjugate: a monoclonal anti-Immunglobulin G (IgG) conjugated porcine Immunglobulin (Ig) was added with a peroxidase enzyme. This anti-IgG was fixed on IgG free epitopes that have not bound to Ag bound to the well and form a complex. Incubate at 37° C. for 1 hour at 70 rpm.
6) Wash and addition of substrate: TMB/DMSO in a citrate/phosphate buffer was used as substrate, and hydrogen peroxide as the reaction catalyst. When the peroxidase enzyme bound to the conjugate recognizes the substrate, it binds to it and the product is transformed by the oxidation action of the hydrogen peroxide into a blue colored product. Incubation took place for 10 minutes at room temperature in the dark.
7) Stop and absorbance reading: the reaction was stopped with sulfuric acid and the colorimetric reading of the corresponding optical densities at 450 nm is recorded:
   In presence of IgG in the serum analyzed an intense yellow colored reaction is observed due to the reaction of the enzyme conjugated to the Anti-IgG Ab which has been bound to the added substrate.
   In the absence of IgG in the serum analyzed, the anti-IgG Ab has not been bound and has been eliminated in subsequent washes. Therefore there is no colorimetric reaction.

The optical density at 450 nm is therefore used as a measure for the amount of specific antibodies against *Brachyspira hyodysenteriae*.

Figure 23:
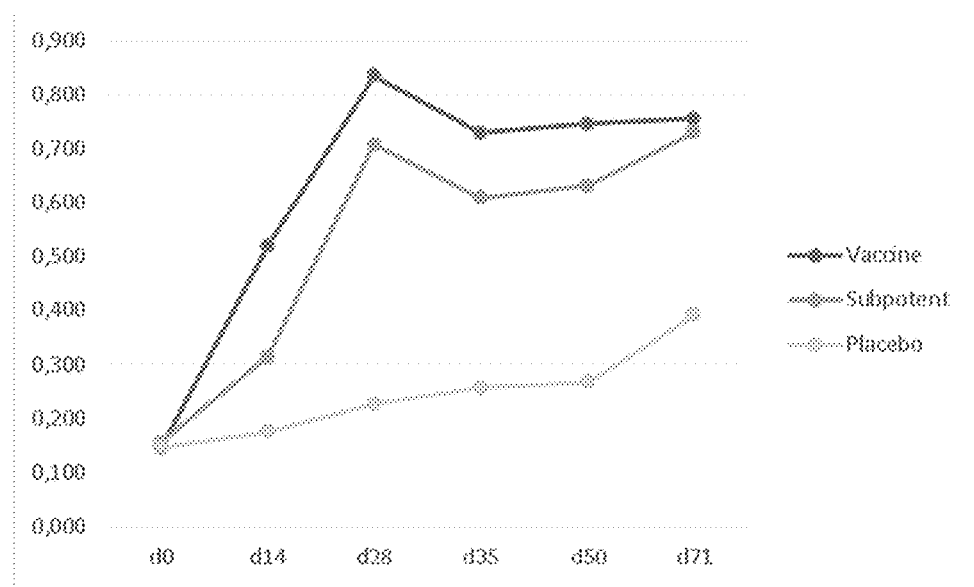
FIG. 23. Specific antibodies in serum after the first vaccination (d0) and subsequent days. The animals received the second shot 14 days after the first vaccination (d14). Dark grey: vaccinated animals; grey: animals vaccinated with subpotent vaccine; light grey: animals treated with placebo.

The results from the ELISA experiments demonstrate that the single strain vaccine of Example 9 elicits an immune response based on antibodies. The results from the ELISA experiments also demonstrate that the single strain vaccine of Example 9 elicits a dose-dependent immune response. The results of the ELISA experiments are shown in FIG. 23.

Culture and Isolation of Strains from Faeces

Aliquots of approximately 5 gram of faeces were collected individually in sterile plastic flasks from all Study groups (A, B, C and D). Between 5-10 gram of faeces were collected from all animals from groups A, B and D at days D35, D41, D43, D45, D48, D50, D52, D56, D59, D64 and D70. Faeces was collected directly from the animals by inducing defecation by palpation if necessary. All faecal samples were cultured in CVS selective media and incubated in anaerobic conditions at 41° C. The signal observed was the haemolysis produced in the culture media and confirmation of the presence of spirochaetes was made by phase contrast microscopy. A negative result was given at seventh day of incubation without haemolysis. All cases in which spirochetes were observed were verified by duplex PCR.

Duplex PCR to Detect *Brachyspira hyodysenteriae* and *Brachyspira pilosicoli*.

Duplex PCRs were used to confirm the presence of *Brachyspira hyodysenteriae* and *Brachyspira pilosicoli* from isolates from swine feces. For this, a DNA fragment of 526 base pairs (bp) of the tlyA gene of *B. hyodysenteriae* and another fragment of 930 bp of the 16S rRNA gene of *B. pilosicoli* was detected with a PCR with specific primers for these fragments. The sequence from which the fragment of the tlyA gene of *B. hyodysenteriae* was amplified has the GenBank entry KU215622.1 and the following sequence (SeqID NO: 17):

>KU215622.1 Brachyspira hyodysenteriae strain 49 TlyA (tlyA) gene, partial cds
GTAAATATGAGAGATAAAGAAAGAAATTCTCTTTCTATAATAAAATCTTT

CCTTGGATTATAATACTAATATAAATGCGATTAGATGAATATGTGCATAG

TGAAGGCTATACAGAAAGCAGATCTAAAGCACAGGATATAATACTAGCCG

GTTGTGTTTTTGTTAATGGAGTAAAGGTAACTTCTAAGGCTCATAAAATA

AAAGATACTGATAATATAGAAGTTGTTCAGAATATAAAATATGTATCAAG

AGCTGGAGAAAAATTAGAAAAGGCGTTTGTAGAATTTGGAATATCTGTAG

AAAATAAAATATGTTTAGATATAGGAGCTTCTACAGGAGGATTTACAGAT

TGTCTGCTTAAGCATGGTGCTAAAAAAGTTTATGCTCTTGATGTAGGACA

TAATCAGCTAGTTTATAAACTTCGTAATGATAATAGGGTAGTGTCAATAG

AAGATTTCAATGCCAAAGATATAAATAAAGAAATGTTCAATGATGAAATC

CCATCTGTAATAGTAAGTGACGTATCATTTATATCAATAACAAAAATAGC

ACCAATCATATTTAAAGAATTAAATAATTTAGAGTTTTGGGTAACTTTAA

TAAAACCACAATTTGAAGCTGAAAGAGGTGATGTTTCAAAAGGCGGTATA

ATACGAGATGATATACTTAGAGAAAAAATATTAAATAATGCTATTTCAAA

GATAATAGACTGCCGATTTAAAGAAGTTAATAGAACCATCTCTCCTATAA

AAGGTGCTAAAGGTAATATAGAATA

For the PCR, the following primers were used:

Bh tlyA_F:
(SeqID NO: 18)
5'-GCA GAT CTA AAG CAC AGG AT-3'

Bh tlyA_R:
(SeqID NO: 19)
5'-GCC TTT TGA AAC ATC ACC TC-3'

The sequence from which the fragment of the 16S rRNA gene of *B. pilosicoli* was amplified has the GenBank entry LC259310.1 (It and the following sequence (SeqID NO: 20):

ATGCAGTCGAGCGGGCTTATTCGGGCAACTGGATAAGTTAGCGGCGAACT

GGTGAGTAACACGTAGGTAATCTGCCGTGAAGTGGGGGATAACCCATGGA

AACATGGACTAATACCGCATATACTCTTGCTACATAAGTAGAGTAGAGGA

AAGTTTTTTCGCTTCACGATGAGCCTGCGGCCTATTAGCCTGTTGGTAGG

GTAATGGCCTACCAAAGCTACGATAGGTAGCCGACCTGAGAGGGTGACCG

GCCACATTGGGACTGAGATACGGCCCAGACTCCTACGGGAGGCAGCAGCT

GAGAATCTTCCACAATGGACGAAAGTCTGATGGAGCGACATCGCGTGAGG

GATGAAGGCCTTCGGGTTGTAAACCTCGGAAATTATCGAAGAATGAGTGA

CAGTAGATAATGTAAGCCTCGGCTAACTACGTGCCAGCAGCCGCGGTAAT

ACGTAGGAGGCAAACGTTGCTCGGATTTACTGGGCGTAAAGGGTGAGTAG

GCGGATTTATAAGTCTAAGGTGAAAGACCGAAGCTCAACTTCGGGAACGC

CTCGGATACTGTAAGTCTTGGATATTGTAGGGGATGATGGAATTCTCGGT

GTAGCGGTGGAATGCGCAGATATCGAGAGGAACACCTATAGCGAAGGCAG

TCATCTGGGCATTTATCGACGCTGAATCACGAAAGCTAGGGGAGCAAACA

GGCTTAGATACCCTGGTAGTCCTAGCCGTAAACGTTGTACACTAGGTGCT

TCTATTTAAATAGGAGTGCCGTAGCTAACGTCTTAAGTGTACCGCCTGAG

GAGTATGCCCGCAAGGGTGAAACTCAAAGAAATTGACGGGTCCCCGCACA

AGTGGTGGAGCATGTGGTTTAATTCGATGATACGCGAAAAACCTTACCTG

GGTTTGAATTGTTAGATGAATGATTTAGAGATAAGTCAGACCGCAAGGAC

GTTTAACATAGGTGCTGCATGGCTGTCGTCAGCTCGTGTCGTGAGATGTT

GGGTTAAGTCCCGCAACGAGCGCAACCCTCACCCTCTGTTGCTAACGAGT

AATGTCGAGCACTCTTAGGGGACTGCCTACGTTCAAGTAGGAGGAAGGTG

GGGATGATGTCAAGTCCTCATGGCCCTTATGTCCAGGGCTACACACGTGC

TACAATGGCAAGTACAAAGAGAAGCAAGACCGCGAGGTGGAGCAAAACTC

AAAAAAGTTGCCTCAGTTCGGATTGGAGTCTGAAACTCGACTCCATGAAG

TTGGAATCACTAGTAATCGTAGATCAGAACGCTACGGTGAATACGTTCCC

GGGGATTGTACACACCGCCCGTCACGCCATCGGAGTTGGTTTTACC

For the PCR, the following primers were used:

Bp16S_F:
(SeqID NO: 21)
5'-CAT AAG TAG AGT AGA GGA AAG TTT TT-3'

Bp16S_R:
(SeqID NO: 22)
5'-CTC GAC ATT ACT CGG TAG CAA CAG-3'

The template DNA for the PCR was extracted from a CVS plate or blood agar plate with the isolated strain (visible hemolysis, without defined surface colonies and visible spirochaetes under the microscope). A sample was taken from the hemolytic zone and inserted into a microtube containing 50 μl of dH$_2$O. The sample was then frozen for 24 hours prior to PCR or boiled for 10-15 minutes. For gram-negative microorganism, these techniques are sufficient to break the cell membrane. After the PCR, the amplified product was visualized by electrophoresis on an agarose gel and the size of the visible fragments was used to identify the presence of *Brachyspira hyodysenteriae* and/or *Brachyspira pilosicoli*. Animals that were positive in duplex PCR were declared as excretory animals.

Figure 22:
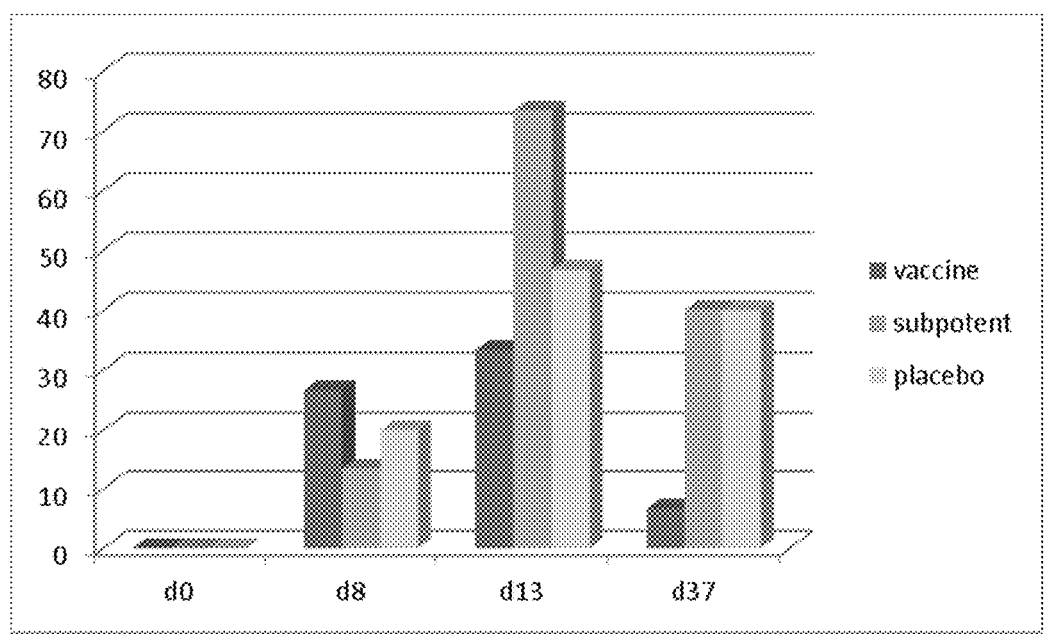
FIG. 22. Shedding: percentage of animals excreting *B. hyodysenteria*. Presence or absence of *Brachyspira* in individual stools was measured by PCR after the 3rd day of the challenge (d0) and at days 8, 13 and 37 (d8, d13, d37). Dark grey: vaccinated animals; grey: animals vaccinated with subpotent vaccine; light grey: animals treated with placebo.

The results are presented in FIG. 22 which shows the percentage of animals shedding *B. hyodysenteria* at different times after the challenge. Shedding (an indication of infection by the challenging strain) is comparable at the beginning of the observation (which indicates that all the groups are equally infected), but it is significantly reduced at the middle and at the end of the observation time in the optimal dose vaccinated group. This is consistent in the reduction of the clinical signs (as measured by the consistency of the stools as indicative of moderate or severe diarrhea) and shows that the vaccine helps the immune system to get rid of the bacteria. This shows that the vaccine of the present invention is effective in controlling infection with *B. hyodysenteria* and furthermore is able to prevent spreading to other individuals.

Faeces and Diarrhoea Evaluation

Stool quality was evaluated in the laboratory on samples collected at different days after the start of the diet change. The classification used in this analysis was 0: normal or loose faeces.
2: liquid diarrhoea
4: Presence of mucus and blood in faeces (typical aspect and smell).

Diarrhoea was evaluated in animals from vaccine, placebo and subpotent vaccine groups.

Figure 20:
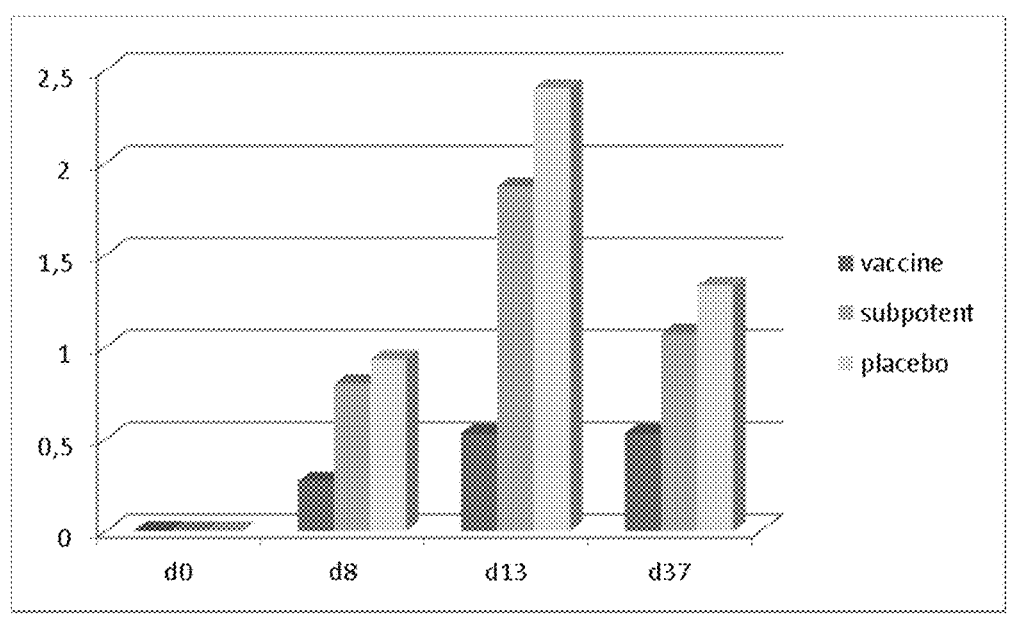
FIG. 20. Average Diarrhea score index. Stool quality was measured using a three score criteria (0, 2, 4) after the 3rd day of the challenge (d0) and at days 8, 13 and 37 (d8, d13, d37). Stool scores were 0 for normal or loose consistency, 2 for liquid diarrhea and 4 for mucous or bloody liquid diarrhea, considered severe diarrhea. Dark grey: vaccinated animals; grey: animals vaccinated with subpotent vaccine; light grey: animals treated with placebo.
Figure 21:
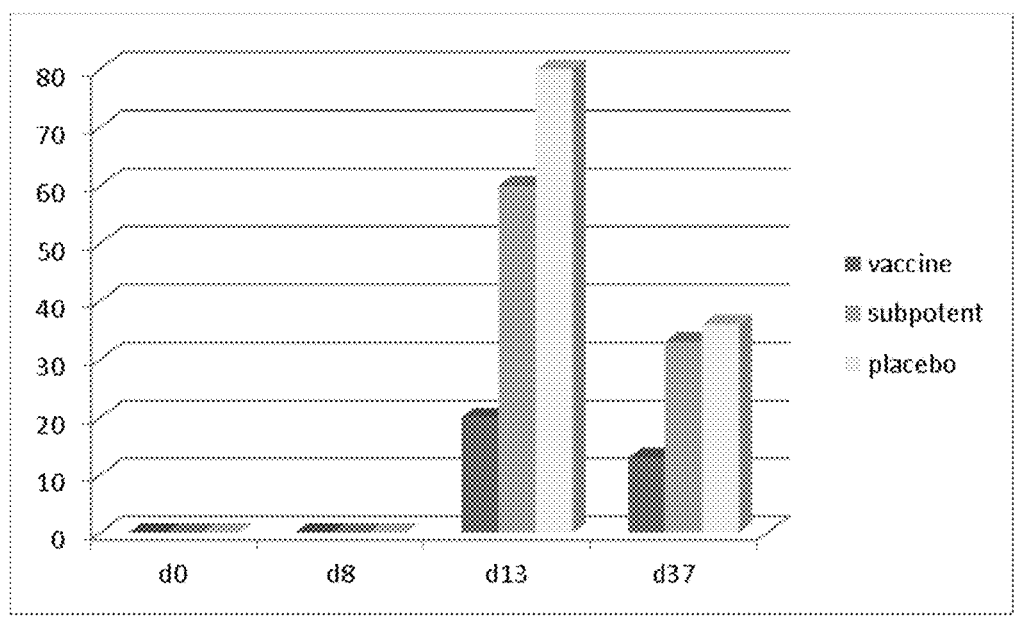
FIG. 21. Percentage of animals with Severe Diarrhea. Stool quality was measured after the 3rd day of the challenge (d0) and at days 8, 13 and 37 (d8, d13, d37). Animals showing mucous or bloody liquid diarrhea were considered to have severe diarrhea. Dark grey: vaccinated animals; grey: animals vaccinated with subpotent vaccine; light grey: animals treated with placebo.

The results are presented in FIGS. 20 and 21, showing the average diarrhoea score index and the percentage of animals with severe diarrhoea in the different groups at different times after the challenge. The figures clearly show that both the average diarrhoea score index as well as the percentage of animals with severe diarrhoea is dramatically lower in animals that have been treated with the potent vaccination of the present invention compared to both the animals treated with a subpotent vaccine or a placebo solution. Treatment with a subpotent vaccine still shows a reduction of both the diarrhoea score index and the fraction of animals with severe diarrhea compared to the animals treated with a placebo solution. This demonstrates that the vaccine of the present invention can be used to prevent and/or treat swine dysentery and remarkably is also effective against a heterologous *B. hyodysenteria* strain.

In general, the vaccinated animals show less diarrhoea, when they develop diarrhoea develop it at later stages, and resolve diarrhoea sooner than non-vaccinated animals or animals vaccinated with a low dose vaccine.

Having thus described the invention in detail, it should be apparent that various modifications and changes can be made without departing from the spirit and scope of the present invention.

All patents, patent applications and publications referred to in the present invention are hereby incorporated by reference in their entirety.

Further Items of the Present Invention

1. A composition comprising bacteria from at least two genetically diverse strains of *Brachyspira hyodysenteriae*.
2. The composition according to item 1, wherein the bacteria are inactivated.
3. The composition according to items 1 and/or 2, wherein the bacteria are present in a concentration of between $10^8$ and $10^9$ of total bacteria/mL.
4. The composition according to one or more of the preceding items, wherein the genetic diversity is conferred by selecting the at least two genetically diverse strains of *Brachyspira hyodysenteriae* from different clonal complexes.
5. The composition according to one or more of the preceding items, wherein at least one strain belongs to clonal complex II, and/or wherein at least one strain belongs to clonal complex V, and/or wherein at least one strain belongs to clonal complex I.
6. The composition according to one or more of the preceding items, wherein the genetically diverse strains are detected in a proportion of at least 1% with respect to the total of detected strains in a region of interest.
7. The composition according to item 6, wherein the region of interest is preferably Spain.
8. The composition according to one or more of the preceding items, wherein the genetically diverse strains belong to the ancestral type from each clonal complex.
9. The composition according to one or more of the preceding items, wherein the composition further comprises a strain which belongs to a third clonal complex, and wherein the third clonal complex is selected from the group consisting of clonal complex I, clonal complex II and clonal complex V.
10. The composition according to one or more of the preceding items, wherein at least one of the strains belong to clonal complex I, at least one of the strains belong to clonal complex II and/or at least one of the strains belong to clonal complex V.
11. The composition according to item 10 wherein at least one of the strains is the strain with deposit number CNCM I-4720, at least one of the strains is the strain with deposit number CNCM I-4721 and/or at least one of the strains is the strain with deposit number CNCM I-4722.
12. The composition according to one or more of the preceding items further comprising an adjuvant, preferably selected from the group consisting of aluminum salts (preferably aluminum hydroxide and/or aluminum phosphate) and mineral oils.
13. The composition according to item 12, wherein the adjuvant is an oil adjuvant, preferably Montanide™ IMS 251 C VG.
14. A composition according to one or more of the preceding items for use as a vaccine, preferably against swine dysentery, wherein the swine dysentery is optionally caused by *Brachyspira hyodysenteriae*.
15. The composition according to item 14, wherein the vaccine is suitable for administration to swine in a region of interest.
16. The composition according to item 15, wherein the region of interest is Spain.
17. The composition according to one or more of items 14 to 16, wherein the vaccine is administered by parenteral administration, preferably by intra-muscular administration.
18. The composition according to one or more of items 14 to 17, wherein the swine are vaccinated two weeks after weaning and, optionally, revaccinated two weeks after the first vaccination.
19. The composition according to one or more of items 15 to 18, wherein the total number of bacteria per dose administrated to swine is between $10^8$ and $10^9$ bacteria, preferably $10^9$ bacteria.
20. A bacteria strain selected from strains deposited at the Collection Nationale de Cultures de Microorganismes (CNCM), Institut Pasteur with registration numbers CNCM I-4720, CNCM I-4721 and CNCM I-4722.
21. A composition for use in the prevention and/or treatment of swine dysentery, said composition comprising a single strain of *Brachyspira hyodysenteriae*, wherein no other *Brachyspira hyodysenteriae* strain is present in the composition, and wherein said strain is the strain with the deposit number CNCM I-4720.
22. A composition for use in a method of reducing the occurrence of mucous and/or bloody diarrhea, said composition comprising a single strain of *Brachyspira hyodysenteriae*, wherein no other *Brachyspira hyodysenteriae* strain is present in the composition, and wherein said strain is the strain with the deposit number CNCM I-4720.
23. A composition for use in a method of delaying the appearance of clinical signs and/or reducing the overall severity of diarrhea and/or swine dysentery, said composition comprising a single strain of *Brachyspira hyodysenteriae*, wherein no other *Brachyspira hyodysenteriae* strain is present in the composition, and wherein said strain is the strain with the deposit number CNCM I-4720.
24. A composition for use in a method of preventing and/or reducing the time of shedding of infective bacteria, said composition comprising a single strain of *Brachyspira hyodysenteriae*, wherein no other *Brachyspira hyodysenteriae* strain is present in the composition, and wherein said strain is the strain with the deposit number CNCM I-4720, wherein optionally the bacteria which shedding is prevented and/or reduced are *Brachyspira hyodysenteriae*.

25. A composition for use in a method of helping to develop diarrhea and/or swine dysentery only at later stages and/or resolving diarrhea and/or swine dysentery sooner when compared to non-vaccinated animals and/or animals vaccinated with a low-dose vaccine, said composition comprising a single strain of *Brachyspira hyodysenteriae*, wherein no other *Brachyspira hyodysenteriae* strain is present in the composition, and wherein said strain is the strain with the deposit number CNCM I-4720.

26. The composition for use according to any of the preceding items, wherein the diarrhea and/or swine dysentery is caused by *Brachyspira hyodysenteriae*.

27. The composition for use according to any of the preceding items, wherein said composition is effective against an infection with *Brachyspira hyodysenteriae* which is of clonal complex II and/or MLVA type 3.

28. The composition for use according to any of the preceding items, wherein said composition is effective against an infection with *Brachyspira hyodysenteriae* which is of another clonal complex and/or another MLVA type than the strain of the composition.

29. The composition for use according to item 24, wherein said composition is effective against two or more strains of *Brachyspira hyodysenteriae* which are of different clonal complexes and/or other MLVA types than the strain of the composition, and which themselves are of a different clonal complex and/or MLVA type.

30. The composition for use according to any of the preceding items, wherein said composition is effective against an infection with *Brachyspira hyodysenteriae* of serotype 2 and/or MLVA type 23.

31. The composition for use according to any of the preceding items, wherein said composition is effective against an infection with *Brachyspira hyodysenteriae* strain B-204, ATCC 31212.

32. The composition for use according to any of the preceding items, wherein the bacteria are inactivated.

33. The composition for use according to any of the preceding items, wherein the bacteria are present in a concentration of at least between $10^8$ and $10^9$ of total bacteria/mL, optionally in a concentration of between $10^8$ and $10^9$ of total bacteria/mL, preferably in a concentration of $5*10^8$ total bacteria/ml.

34. The composition for use according to any of the preceding items, wherein the administered dosage is between 1 mL to 5 mL, optionally 2 mL.

35. The composition for use according to any of the preceding items, wherein the bacteria are present in an amount of between $10^7$ and $10^{11}$ of total bacteria/dose, between $10^8$ and $10^{10}$ of total bacteria/dose, preferably in an amount of $10^9$ of total bacteria/dose.

36. The composition for use according to any of the preceding items, further comprising an adjuvant selected from the group consisting of aluminum salts and mineral oils, optionally wherein the adjuvant is an oil adjuvant.

37. The composition for use according to any of the preceding items, wherein the composition does not comprise an adjuvant 38. The composition for use according to any of the preceding items, wherein the composition does not comprise Thiomersal and/or mercurial derivatives and/or heavy metals.

39. The composition for use according to any of the preceding items, wherein the composition is administered by parenteral administration.

40. The composition for use according to any of the preceding items, wherein the composition is administered between one and three weeks after weaning, optionally wherein the composition is administered two weeks after weaning.

41. The composition for use according to any of the preceding items, wherein the animals are revaccinated two weeks after the first vaccination.

42. The composition for use according to any of the preceding items, wherein the prevention and/or treatment comprises two administrations, optionally wherein the prevention and/or treatment consists of two administrations.

43. The composition for use according to any of the preceding items, wherein the prevention and/or treatment is effective three weeks after the last administration and/or five weeks after the first administration.

44. The composition for use according to any of the preceding items, wherein the prevention and/or treatment is effective 10 weeks after the first administration and/or 8 weeks after the last administration.

45. The composition for use according to any of the preceding items, wherein the prevention and/or treatment is effective for at least 5 weeks.

46. The composition for use according to any of the preceding items, wherein the prevention or treatment is a prevention or treatment of a pig, preferably of a domestic pig.

47. The composition for use according to the previous item, wherein the prevention or treatment is also effective when the pig is fed with a hyperproteic feed, optionally wherein said hypoproetic feed comprises 50% soya.

48. The composition for use according to any of the preceding items, wherein administering the composition does not have a negative influence on body weight gain in a healthy animal, optionally wherein said body weight gain is the body weight gain within 35 days after administration.

49. The composition for use according to any of the preceding items, wherein administering the composition does not result in an increased rectal temperature 48 hours after the administration, and/or does not result in an increased rectal temperature 24 hours after the administration.

50. The composition for use according to any of the preceding items, wherein the prevention and/or treatment over the lifespan of the animal does in total not amount to more than 72 hours of increased rectal temperature compared to a non-treated animal.

51. The composition for use according to any of the preceding items, wherein the prevention and/or treatment over the lifespan of the animal does in total not amount to more than 48 hours of increased rectal temperature compared to a non-treated animal.

52. The composition for use according to any of items 49 to 51, wherein said increase in rectal temperature is an increase of more than 0.5° C.

53. The composition for use according to any of the preceding items, wherein no local reactions at the injection site are present for at least 14 days after each administration of the composition.

54. The composition for use according to any of the preceding items, wherein no signs of abnormal behavior and/or systemic reactions are present for at least 14 days after each administration of the composition, optionally wherein said signs of abnormal behavior and/or systemic reactions are any one of dyspnoea, mucus, cough, diarrhoea, vomit, paralysis, motile dysfunctions, somnolence, depression and external appearance.

55. A composition for use in a method of reducing the shedding of infective bacteria comprising the administration of the composition according to any of the preceding items, optionally wherein said bacteria are *Brachyspira hyodysenteriae*.

56. A vaccine comprising any of the above mentioned compositions.

57. A method of treating and/or preventing diarrhea in an animal using any of the compositions and/or vaccines of the previous items, wherein optionally said diarrhea is mucous and/or bloody diarrhea.

58. A method of reducing the occurrence of mucous and/or bloody diarrhea in an animal using any of the compositions and/or vaccines of items 21-57.

59. A method of treating and/or preventing swine dysentery in an animal using any of the compositions and/or vaccines of items 21-57.

60. A method of delaying the appearance of clinical signs and/or reducing the overall severity of diarrhea and/or swine dysentery in an animal using any of the compositions and/or vaccines of items 21-57.

61. A method of preventing and/or reducing the time of shedding of *Brachyspira hyodysenteriae* in an animal using any of the compositions and/or vaccines of items 21-57.

62. A method of helping to develop diarrhea and/or swine dysentery only at later stages and/or resolving diarrhea and/or swine dysentery sooner when compared to non-vaccinated animals and/or animals vaccinated with a low-dose vaccine in an animal using any of the compositions and/or vaccines of items 21-57.

The invention claimed is:

1. A method of eliciting an immune response against *Brachyspira hyodysenteriae* in an animal comprising administering to said animal a composition comprising a dose of a single strain of *Brachyspira hyodysenteriae*, wherein no other *Brachyspira hyodysenteriae* strain is present in the composition, wherein the single strain is the strain of *Brachyspira hyodysenteriae* deposited at the Collection Nationale de Cultures de Microrganismes (CNCM), Institut Pasteur under the registration number CNCM I-4720, wherein the *Brachyspira hyodysenteriae* strain is inactivated.

2. The method of claim 1, wherein the animal is a pig.

3. The method of claim 1, wherein the *Brachyspira hyodysenteriae* strain in the composition is inactivated by formaldehyde.

4. The method of claim 1, wherein the *Brachyspira hyodysenteriae* strain in the composition is present at a concentration of $10^7$ to $10^{12}$ of the bacteria per mL dose.

5. The method of claim 1, wherein the composition comprises an adjuvant.

6. The method of claim 1, wherein the composition is administered to the animal by parenteral administration.

7. The method of claim 6, wherein the parenteral administration is intramuscular administration.

8. The method of claim 2, wherein the immune response elicited by the composition in the animal is against swine dysentery or diarrhea caused by *Brachyspira hyodysenteriae*.

9. The method of claim 2, wherein the immune response elicited by the composition delays the appearance of clinical signs of or delays the overall severity of swine dysentery and/or diarrhea caused by *Brachyspira hyodysenteriae* in said animal.

10. The method of claim 2, wherein the immune response elicited by the composition reduces the occurrence of mucous and/or bloody diarrhea caused by *Brachyspira hyodysenteriae* in said animal.

* * * * *